United States Patent
Mah et al.

(10) Patent No.: US 11,371,999 B2
(45) Date of Patent: Jun. 28, 2022

(54) ASSAY FOR DETERMINING THE TOTAL CARBONYLATION LEVEL ON A POLYPEPTIDE

(71) Applicants: Genentech, Inc., South San Francisco, CA (US); University of Kansas, Lawrence, KS (US)

(72) Inventors: Anna Mah, San Francisco, CA (US); Christian Schoeneich, Lawrence, KS (US); Yi Yang, El Cerrito, CA (US); Di Gao, Clarksburg, MD (US); Lynn A. Gennaro, San Mateo, CA (US)

(73) Assignees: University of Kansas, Lawrence, KS (US); Genentech, Inc., South San Franciso (CA)

( * ) Notice: Subject to any disclaimer, the term of this patent is extended or adjusted under 35 U.S.C. 154(b) by 171 days.

(21) Appl. No.: 16/195,409

(22) Filed: Nov. 19, 2018

(65) Prior Publication Data

US 2019/0219590 A1 Jul. 18, 2019

Related U.S. Application Data

(63) Continuation of application No. PCT/US2017/033371, filed on May 18, 2017.

(60) Provisional application No. 62/338,605, filed on May 19, 2016.

(51) Int. Cl.
| | |
|---|---|
| G01N 33/68 | (2006.01) |
| G01N 33/58 | (2006.01) |
| G01N 33/50 | (2006.01) |
| G01N 33/533 | (2006.01) |

(52) U.S. Cl.
CPC ....... *G01N 33/6842* (2013.01); *G01N 33/502* (2013.01); *G01N 33/533* (2013.01); *G01N 33/582* (2013.01); *G01N 2440/00* (2013.01)

(58) Field of Classification Search
CPC ............. G01N 2440/00; G01N 33/502; G01N 33/533; G01N 33/582; G01N 33/68; G01N 33/6842; Y10T 436/200833; Y10T 436/25; Y10T 436/25125; Y10T 436/25375
USPC ... 436/547, 548, 86, 89, 128, 161, 174, 175, 436/177; 422/70, 527, 534; 435/7.1, 7.8
See application file for complete search history.

(56) References Cited

U.S. PATENT DOCUMENTS

| | | | | |
|---|---|---|---|---|
| 5,362,852 A | * | 11/1994 | Geoghegan | C07K 14/5421 530/328 |
| 2009/0004684 A1 | * | 1/2009 | Maier | G01N 33/6803 435/23 |
| 2010/0105102 A1 | | 4/2010 | Hanes et al. | |
| 2010/0254581 A1 | | 10/2010 | Neeser et al. | |
| 2011/0039277 A1 | * | 2/2011 | Mastroberardino | G01N 33/542 435/7.1 |
| 2012/0309040 A1 | * | 12/2012 | Madian | G01N 33/6848 435/23 |

FOREIGN PATENT DOCUMENTS

| | | |
|---|---|---|
| CN | 101228125 A | 7/2008 |
| CN | 104020246 A | 9/2014 |
| WO | 2007/014839 A2 | 2/2007 |
| WO | 2012/175519 A1 | 12/2012 |

OTHER PUBLICATIONS

Yang et al. Journal of Pharmaceutical Sciences, vol. 107, Jun. 21, 2018, pp. 2570-2580.*
Bai et al., "Role of iron and sodium citrate in animal protein-free CHO cell culture medium on cell growth and monoclonal antibody production" Biotechnol Prog 27(1):209-219 ( 2011).
Buss et al., "Protein carbonyl measurement by a sensitive ELISA method" Free Radic Biol Med 23(3):361-366 ( 1997).
International Search Report for International Patent Application No. PCT/US2017/033371 completed on Jun. 28, 2017.
Halliwell et al., "Hydrogen peroxide. Ubiquitous in cell culture and in vivo?" IUBMB Life 50:251-257 ( 2000).
Hawe et al., "Fluorescent molecular rotors as dyes to characterize polysorbate-containing IgG formulations" Pharm Res 27(2):314-326 ( 2010).
Jaeger et al., "Peroxide accumulation in detergents" J Biochem Biophys Methods 29(1):77-81 ( 1994).
Keener et al., "Optimization of oxidized antibody labeling with Lucifer Yellow CH" Biotechniques 16(5):894-897 ( 1994).
Levine et al., "Determination of carbonyl content in oxidatively modified proteins" Methods Enzymol 186:464-478 ( 1990).
Mallaney et al., "Effect of ambient light on monoclonal antibody product quality during small-scale mammalian cell culture process in clear glass bioreactors" Biotechnol Prog 30(3):562-570 ( 2014).
Matthijssens et al., "Evaluation of different methods for assaying protein carbonylation" Current Analytical Chemistry 3(2):93-102 ( 2007).
Mesquita et al., "Simplified 2,4-dinitrophenylhydrazine spectrophotometric assay for quantification of carbonyls in oxidized proteins" Analytical Biochem 458:69-71 ( 2014).
Mohanty et al., "A fluorimetric semi-microplate format assay of protein carbonyls in blood plasma" Analytical Biochem 400(2):289-294 ( 2010).
Morehead et al., "Optimization of oxidation of glycoproteins: An assay for predicting coupling to hydrazide chromatographic supports" J Chromatography A 587(2):171-176 (Dec. 20, 1991).
Rogowska-Wrzesinska et al., "Analysis of protein carbonylation—pitfalls and promise in commonly used methods" Free Radic Res 48(10):1145-1162 ( 2014).
Stadtman et al., "Metal ion-catalized oxidation of proteins: biochemical mechanism and biological consequences" Free Radic Biol Med 9(4):315-325 ( 1990).
Uehara et al., "Metal-mediated protein oxidation: Applications of a modified Elisa-based carbonyl detection assay for complex proteins" Pharm Res 32(2):691-701 ( 2015).

(Continued)

Primary Examiner — Maureen Wallenhorst
(74) Attorney, Agent, or Firm — Charles Wong

(57) ABSTRACT

The description relates to a method and kits for determining the total carbonylation level on a polypeptide.

14 Claims, 15 Drawing Sheets

(56) References Cited

OTHER PUBLICATIONS

Yan et al., "Chemical probes for analysis of carbonylated proteins: A review" J Chromatogr B Analyt Technol Biomed Life Sci 879(17-18):1308-1315 (2011).

Zhou et al., "Biologics formulation factors affecting metal leachables from stainless steel" AAPS PharmSciTech 12(1):411-421 (Mar. 2011).

Tamarit, J. et al., "Analysis of oxidative stress-induced protein carbonylation using fluorescent hydrazides" Journal of Proteomics 75(12):3778-3788 (2012).

* cited by examiner

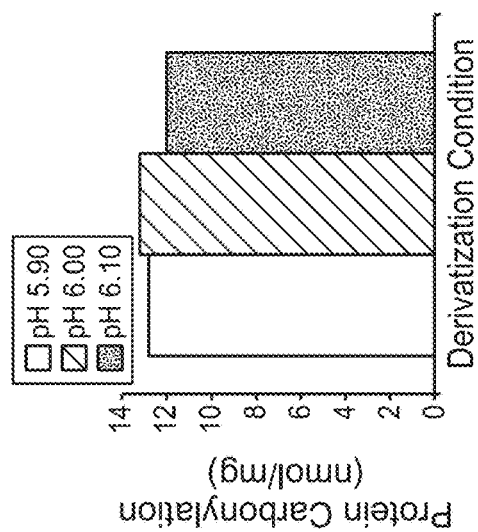
FIG. 7C
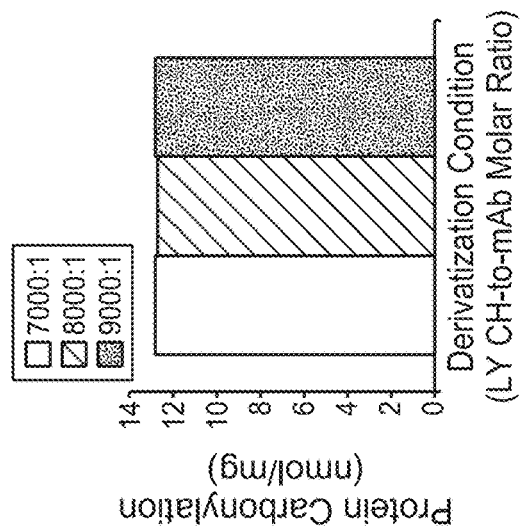
FIG. 7B
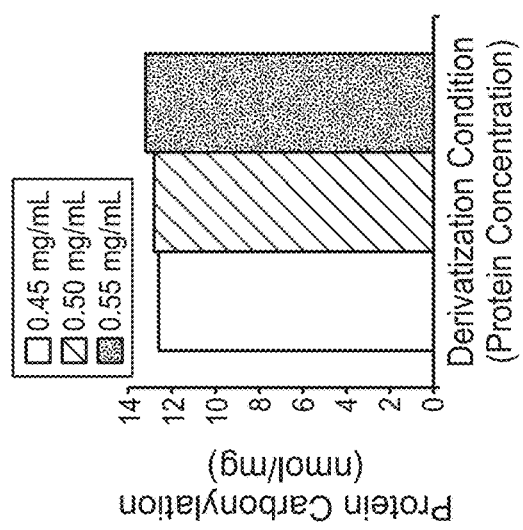
FIG. 7A
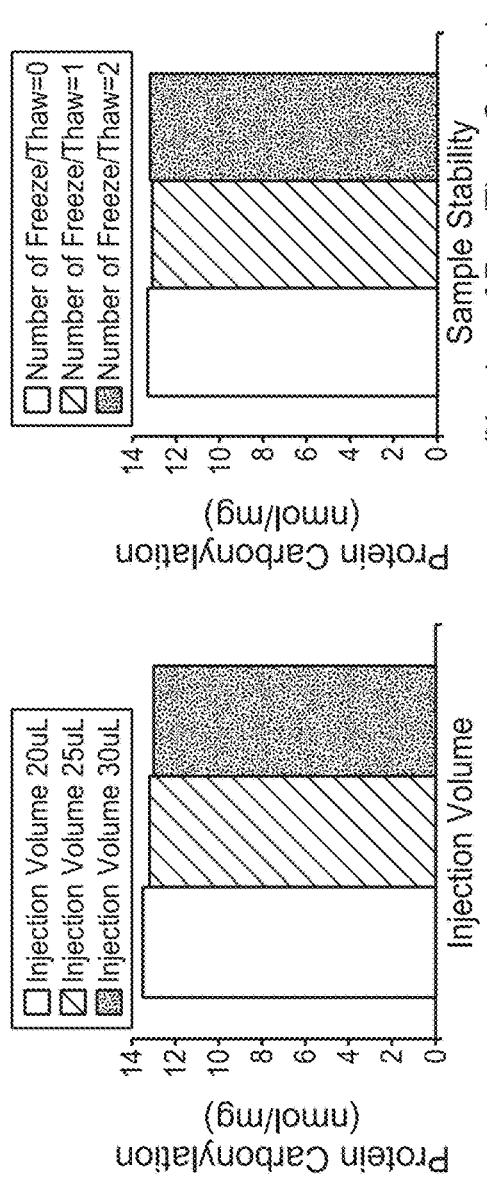
FIG. 7F
FIG. 7E
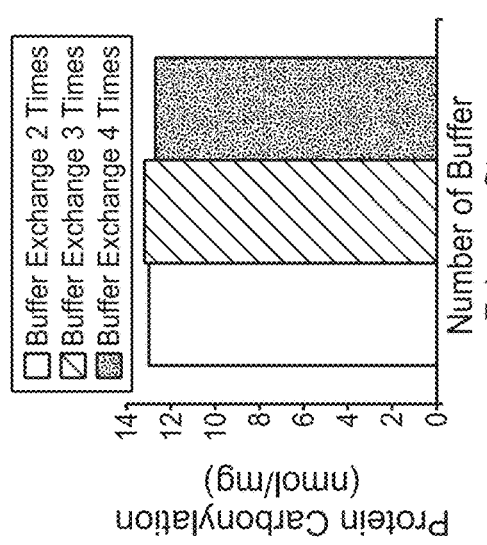
FIG. 7D

ASSAY FOR DETERMINING THE TOTAL CARBONYLATION LEVEL ON A POLYPEPTIDE

CROSS-REFERENCE TO RELATED APPLICATIONS

This application is a continuation of International Patent Application No. PCT/US2017/033371, having an international filing date of May 18, 2017, the entire contents of which are incorporated herein by reference, and which claims benefit of priority to U.S. Patent Application No. 62/338,605 filed on May 19, 2016, which is herein incorporated by reference in its entirety.

FIELD OF THE INVENTION

The present description relates to a method for determining the total carbonylation level on a polypeptide.

BACKGROUND

Metal-catalyzed oxidation products are a highly relevant quality attribute of monoclonal antibodies (mAbs) due to the contact of the mAbs with metal or metal ions during the manufacturing or storage process. During purification or storage, stainless steel is a common surface contact material. The iron ions present in the cell culture media or leached from the stainless steel can cause methionine and histidine oxidation in the Fc region of the mAb. Other than methionine and histidine oxidation, protein carbonylation, referring to the formation of aldehyde/ketone groups in proteins, is a major degradation pathway from the metal-catalyzed oxidation reaction and has not been studied extensively on mAbs. As the result of the oxidative carbonylation, the positive charge on lysine and arginine side chains and the steric constrain from proline residue are lost. Those changes could lead to increased protein aggregation propensity and thus potentially affects mAb product quality and stability profiles. In addition, the mAb aggregates induced by metal-catalyzed oxidation can be more immunogenic in transgenic mice than those induced by other stress conditions. Therefore, it is of significant importance to identify the extent of carbonylation of mAbs from metal-catalyzed oxidation during manufacturing and storage.

For quantitative measurement of total protein carbonylation levels, different hydrazides have been adopted as the derivatization reagents to react with the carbonyl groups on proteins (Yan et al., 2011). Quantitation was usually based on the unique characteristic of the hydrazides and the corresponding hydrazones after the derivatization. For example, a widely used spectrophotometric carbonylation assay measures the absorbance of a derived sample at 375 nm, where the derivatization reagent, 2,4-dinitrophenylhydrazine (DNPH), and the resulting hydrazone, strongly absorb (Levine et al., 1990). A fluorometric carbonylation assay measures the fluorescence with excitation at 485 nm and emission at 535 nm of a derived sample after the derivatization by fluorescein thiosemicarbazide (Mohanty et al., 2010). An ELISA carbonylation assay uses an anti-DNPH antibody for quantification after the derivatization of a sample by DNPH (Buss et al., 1997). While different hydrazide reagents have been employed for the derivatization and quantitation purposes, a common procedure in the protein carbonylation assays is the removal of the unbound hydrazide after the derivatization step to prevent over-quantification of the carbonylation levels (Rogowska-Wrzesinska et al., 2014). Typically, the unbound hydrazide is removed through protein precipitation and washing, which is a labor-intensive process and constitutes a major source of experimental variability. In fact, it was demonstrated that two additional washing steps reduced the carbonylation result by 15% when using the spectrophotometric carbonylation assay with DNPH (Matthijssens et al., 2007). The large assay variability and the labor-intensive nature associated with the washing step can make it difficult to broadly apply these carbonylation assays to measure mAb carbonylation during product development. Modified ELISA (Uehara et al., 2015) and DNPH (Mesquita et al., 2014) assays have been reported recently using simplified methodologies. However, these modified methods are still relatively labor-intensive and their robustness was not assessed yet. Lucifer Yellow carbohydrazide (LY-CH) has previously been used as a derivatization reagent to quantify aldehyde groups formed by periodic acid oxidation on the N-Glycan oligosaccharide residues of antibodies (Morehead et al., 1991). An assay was described to examine the quantitative labeling of oxidized antibody carbohydrate residues with LY-CH (Keener et al., 1994). In this assay, the LY-CH-to-polypeptide molar ratio in the derivatization reaction is limited due to the use of conventional buffer systems and results in a more difficult removal of unbound LY-CH. Furthermore, the assay does not correct the protein contribution to the respective absorbance of the hydrazide reagent for quantifying the carbonyl content which leads to an overestimation of the carbonylation content.

US 2006/0216756 A1 discloses a method for two-dimensional evaluation of the nature of oxidized protein, the method comprises the steps of specific fluorescent labeling of the carbonyl groups of the oxidized protein in a horny layer specimen taken from skin. US 2007/0110670 A1 discloses methods comprising the labeling of carbonyl groups of an oxidized protein with a fluorescence dye for evaluating hair damage. WO2012175519 A1 describes a method for detecting and/or quantifying protein carbonyl groups in at least one protein-containing sample comprising the steps of labeling protein carbonyl groups with hydrazide followed by an analysis of the sample using one-dimensional or two-dimensional gel electrophoresis.

In the present description, a simplified, more robust and more accurate protein Carbonylation Assay using Lucifer Yellow carbohydrazide (CALY) is described which overcomes the problems of the prior art as described above.

SUMMARY

The description relates to a method and kits for determining the total carbonylation level on a polypeptide.

In one aspect, the description relates to a method for determining the total carbonylation level on a polypeptide wherein the method comprises the steps of a) contacting the polypeptide in a solution with a hydrazide dye under conditions such that the hydrazide dye can react with the carbonyl groups present on the amino acid residues of the polypeptide to form a polypeptide-dye-complex, b) removing unbound hydrazide dye from the resultant solution from step a), c) determining in the resultant solution from step b) the concentration of the hydrazide dye bound in the polypeptide-dye-complex and the concentration of the polypeptide bound in the polypeptide-dye-complex, and d) determining the total carbonylation level of the polypeptide based on the ratio of the concentration of the hydrazide dye bound in the polypeptide-dye-complex to the concentration of the polypeptide bound in the polypeptide-dye-complex.

In one embodiment, the hydrazide dye is LY-CH. In one embodiment, step a) is performed in the presence of alkali metal ions. In one embodiment, the amino acid residues of the polypeptide are selected from the group consisting of arginine, lysine, proline and threonine. In one embodiment, the polypeptide is an antibody. In one embodiment, the antibody is a polyclonal antibody, a monoclonal antibody, a humanized antibody, a human antibody, a chimeric antibody, a multi-specific antibody, an antibody fragment, an antibody drug conjugate, a THIOMAB™ or a THIOMAB™ drug conjugate. In one embodiment, the polypeptide and the hydrazide dye is contacted in step a) in a final molar ratio of 6,000-10,000. In one embodiment, step a) is performed in the presence of a non-ionic surfactant. In one embodiment, the non-ionic surfactant is reduced Triton X-100. In one embodiment, step a) is performed at a temperature of 35° C.-39° C. In one embodiment, step a) is performed for 10-20 h. In one embodiment, step b) is performed by a method selected from the group consisting of filtration, gel filtration and dialysis. In one embodiment, step b) is performed by filtration. In one embodiment, filtration is carried out in the presence of 100-300 mM potassium phosphate and in the presence of 200-300 mM potassium chloride.

In another aspect, the description relates to a kit for carrying out the method as described herein, wherein the kit comprises hydrazide dye and a buffer. In one embodiment, the hydrazide dye is LY-CH. In one embodiment, the buffer is lithium MES buffer. In one embodiment, the kit further comprises a non-ionic surfactant, a standard for the polypeptide and a standard for hydrazide dye. In one embodiment, the non-ionic surfactant is reduced Triton X-100.

BRIEF DESCRIPTION OF THE FIGURES

FIG. 7A shows the robustness assessment of the CALY assay, specifically the mAb concentration for the derivatization reaction.

FIG. 7B shows the robustness assessment of the CALY assay, specifically the molar ratio for the derivatization reaction.

FIG. 7C shows the robustness assessment of the CALY assay, specifically the pH values for the derivatization reaction.

FIG. 7D shows the robustness assessment of the CALY assay, specifically the number of buffer exchange (by filtering) steps.

FIG. 7E shows the robustness assessment of the CALY assay, specifically the injection volume.

FIG. 7F shows the robustness assessment of the CALY assay, specifically the sample stability against the number of freeze/thaw cycles.

DETAILED DESCRIPTION OF EMBODIMENTS OF THE INVENTION

I. DEFINITIONS

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

The term "about" as used herein refers to the usual error range for the respective value readily known to the skilled person in this technical field. Reference to "about" a value or parameter herein includes (and describes) embodiments that are directed to that value or parameter per se.

The term "antibody" herein is used in the broadest sense and encompasses various antibody structures, including but not limited to monoclonal antibodies, polyclonal antibodies, multispecific antibodies (e.g., bispecific antibodies), antibody fragments so long as they exhibit the desired antigen-binding activity, a humanized antibody, a human antibody, a chimeric antibody, an antibody drug conjugate, a THIOMAB™ and a THIOMAB™ drug conjugate.

Figure 1:
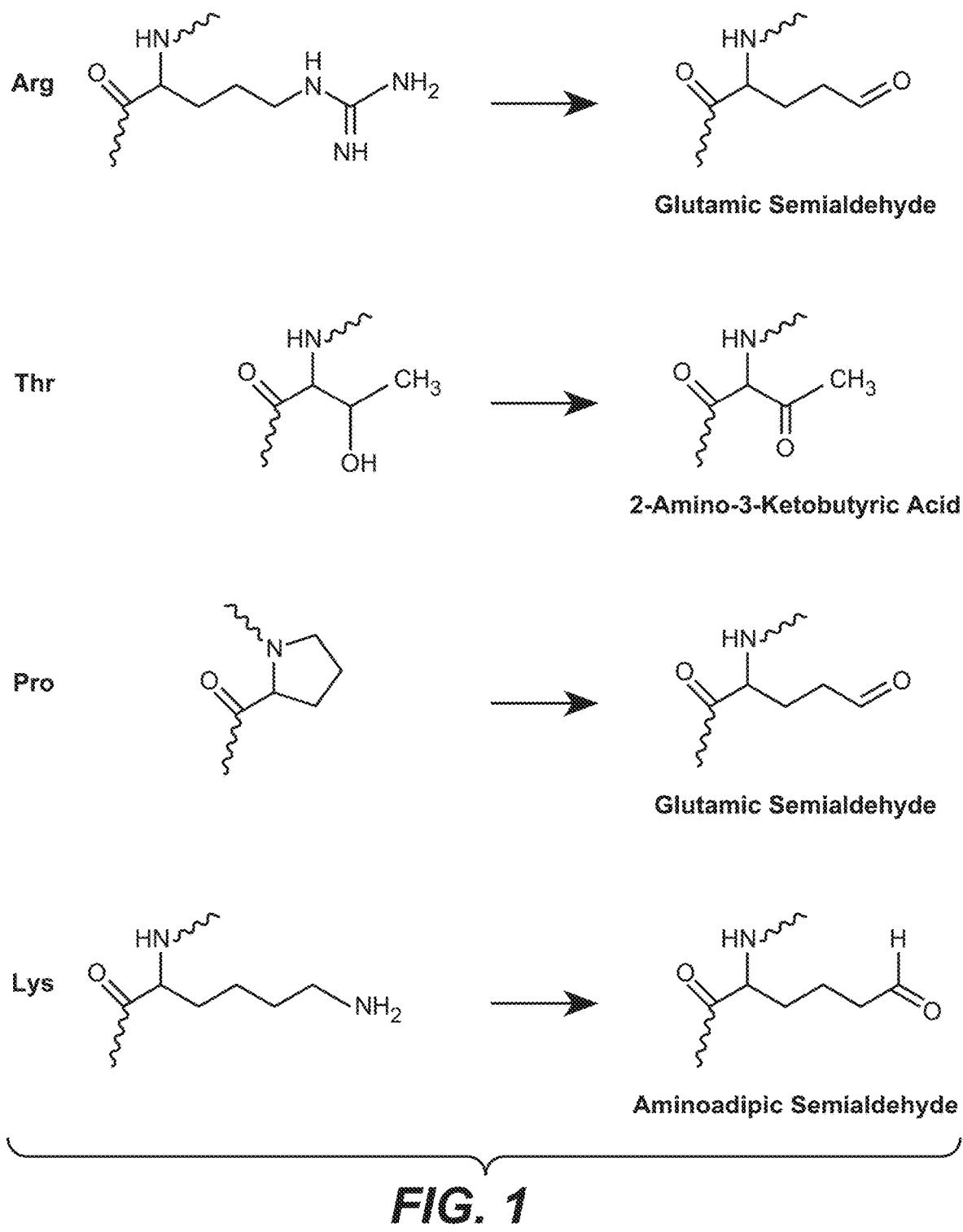
FIG. 1 shows the major carbonylation products from metal-catalyzed oxidation.

The term "carbonylation" as used herein refers to the formation of aldehyde or ketone groups on amino acid residues in polypeptides, e.g. as shown in FIG. 1. The term "total carbonylation level" as used herein refers to the amount of carbonyl groups (in nmol) per unit amount (in nmol or mg) of polypeptide.

Figure 2A:
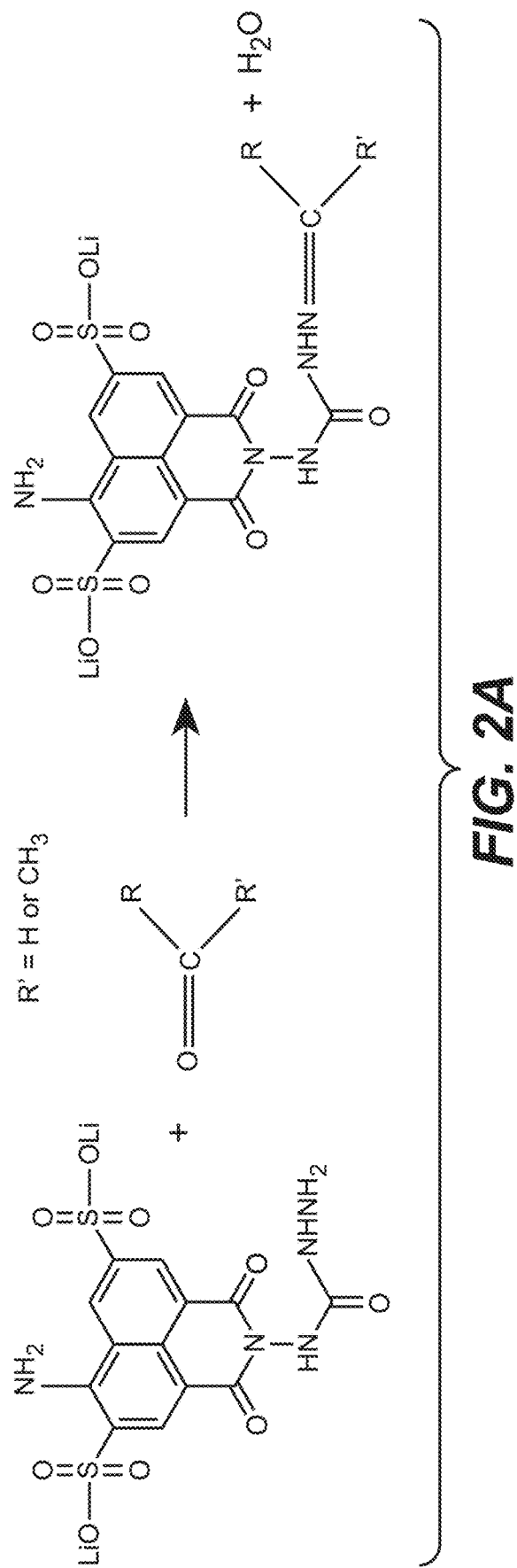
FIG. 2A shows the derivatization reaction between LY-CH and the carbonyl group.

The term "derivatization" as used herein refers to a chemical reaction that changes the chemical nature of an amino acid or polypeptide, while leaving the amino acid or polypeptide backbone structure unchanged. Specifically, herein LY-CH is used in the chemical reaction as shown in FIG. 2A to chemically modify the carbonyl group on an amino acid or polypeptide such that a polypeptide-dye-complex is formed (by the reaction between the hydrazide group on Lucifer Yellow carbohydrazide and the carbonyl group on polypeptides that forms the Schiff base as shown in FIG. 2A).

Figure 3A:
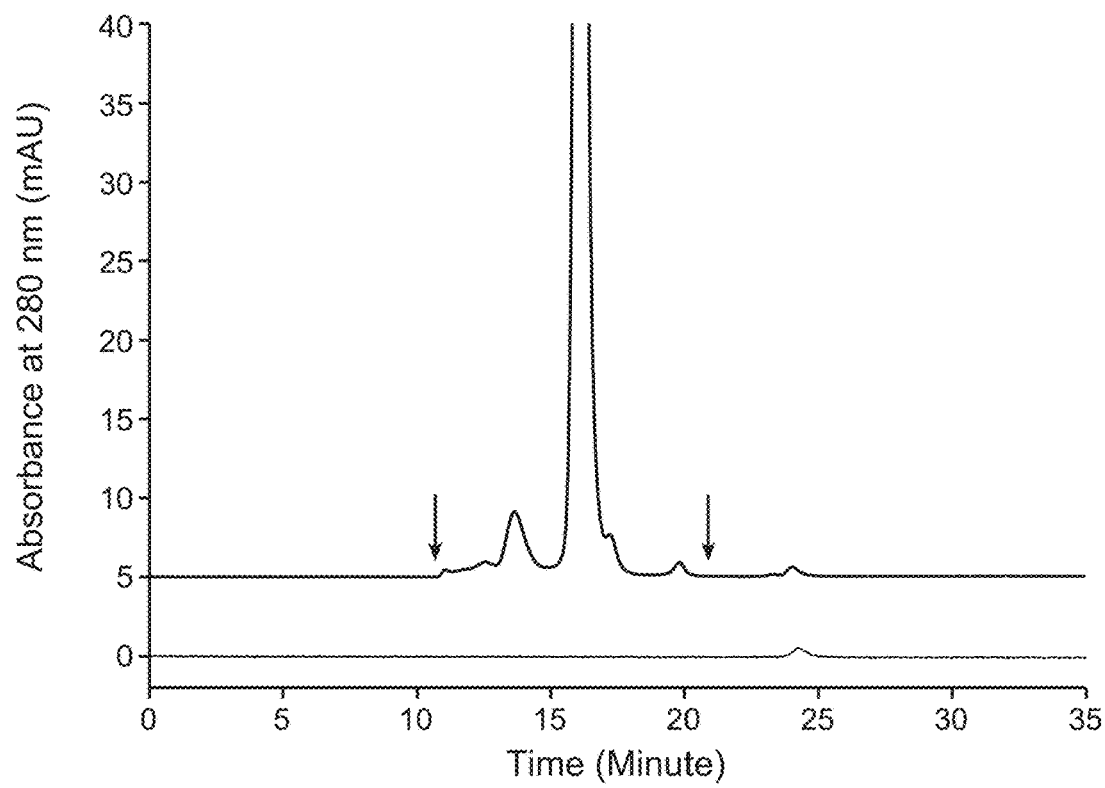
FIG. 3A shows the size exclusion chromatograms, with absorbance at 280 nm of a LY-CH derived-mAb sample (arrows showing the start and the end of the peak integration), and of the buffer blank (lower profile).
Figure 3B:
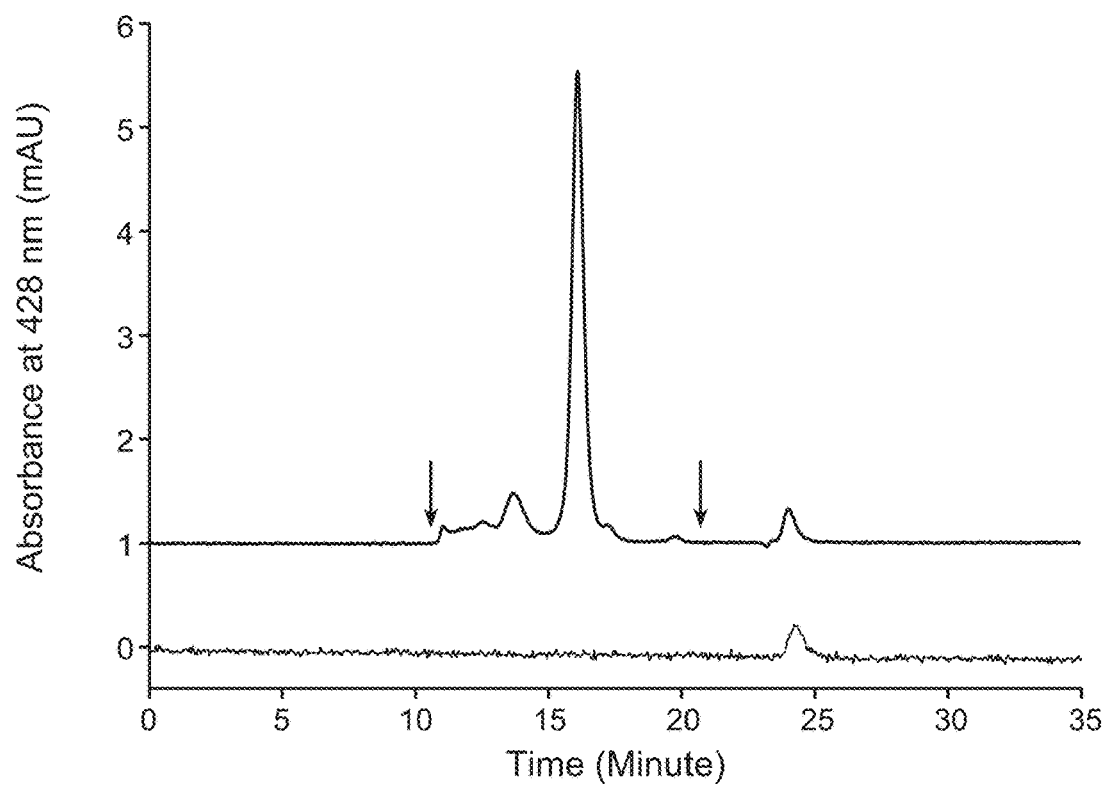
FIG. 3B shows the size exclusion chromatograms, with absorbance at 428 nm, of a LY-CH derived-mAb sample (arrows showing the start and the end of the peak integration), and of the buffer blank (lower profile).

The term "integrated absorbance peak area" as used herein refers to the area under the curve in a chromatogram measured for a specific analyte at a specific wave length. For example, FIG. 3 shows the size exclusion chromatograms with absorbance at 280 nm (FIG. 3A) and 428 nm (FIG. 3B) of a LY-CH derived-mAb sample. The arrows show the start and end points for the peak integration. The integrated absorbance peak area in FIG. 3 is the area under the curve in between the start and end points.

The term "linear regression fitting" is used herein as described in Yan, X., Gang Su, X. (2009), Linear Regression Analysis: Theory and Computing, World Scientific.

The terms "Lucifer Yellow", "Lucifer Yellow carbohydrazide", "Lucifer Yellow CH", "LY" or "LY-CH" as used herein refer to the unbound and/or bound form of Lucifer Yellow. Lucifer Yellow is a water-soluble dye with strong absorbance of electromagnetic radiation at 280 nm and 428 nm. The term "polypeptide-dye-complex" as used herein refers to a polypeptide which reacted with a hydrazide dye thereby forming a polypeptide-dye-complex. Specifically, the term "polypeptide-dye-complex" as used herein refers to a polypeptide which reacted with LY-CH as described above. The term "unbound hydrazide dye" specifically refers to a hydrazide dye as used herein as derivatization reagent, i.e. which is not bound in a polypeptide-dye-complex. The term "unbound LY-CH" specifically refers to LY-CH as used herein as derivatization reagent, i.e. which is not bound in a polypeptide-dye-complex. The terms "Lucifer Yellow", "Lucifer Yellow carbohydrazide", "Lucifer Yellow CH", "LY" or "LY-CH" can be used interchangeably. LY-CH as used herein is used as LY-CH dilithium salt.

The term "hydrazide dye" as used herein refers to dye comprising a hydrazide as a functional group. The general structure for a hydrazide dye is E-N(R)—N(R)$_2$, wherein R can be hydrogen and E is a dye. The term "dye" refers to a molecule or moiety that absorbs electromagnetic radiation, e.g. at a wavelength of 428 nm.

The term "molar ratio" as used herein refers to the ratio of amount LY-CH (in mole) used over the amount of polypeptide (in mole) in the derivatization reaction as described herein.

The term "nominal molecular weight limit" of a filter unit as used herein refers to the pore size of a filter unit by which at least 90% of a solute of a specific molecular weight is retained e.g. a filter unit with a nominal molecular weight limit of 30 kDa retains at least 90% of a solute with a molecular weight of 30 kDa.

The term "non-ionic surfactant" as used herein refers to a non-ionic agent which has the ability to lower the surface tension between two liquids or between a liquid and a solid. Examples for non-ionic surfactants are Nonidet P-40, Poloxamer 188, Polysorbate 20, Polysorbate 80, Triton X-100, reduced Triton X-100, Tween 20 and Tween 80. The term "reduced Triton X-100" as used herein relates to Triton X-100 in which the benzene ring has been reduced to a cyclohexane ring. Due to the benzene ring, the unreduced Triton X-100 has an absorption spectrum which overlaps with the absorption spectrum of polypeptides (260 nm-280 nm). The reduction to a cyclohexane ring makes the Triton X-100 suitable for the analysis of polypeptides as no overlap of the absorption spectra of the Triton X-100 and the polypeptide occurs.

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

II. METHODS

In the present description, a simplified, more robust and more accurate protein carbonylation assay for measuring the total carbonylation level of a polypeptide is provided. As mentioned before, removal of unbound hydrazide through protein precipitation and washing is a labor-intensive process and constitutes a major source of the experimental variability, e.g. due to sample loss. LY-CH was selected as derivatization reagent since it has a relatively high solubility in water (~200 mM) and is significantly more hydrophilic than many hydrazide reagents such as DNPH. The soluble and hydrophilic nature of LY-CH enables the removal of the unbound LY-CH by a buffer exchange filtering process which leads to an excellent sample recovery. In the present description, the solubility of LY-CH was further improved by using lithium hydroxide for the buffer preparation. The improved solubility of LY-CH based on the presence of lithium ions in the improved buffer allows the use of a higher LY-CH-to-polypeptide molar ratio for the derivatization reaction and an easier removal of the residual LY-CH reagent after the derivatization as compared to conventional buffer systems. Another advantage of LY-CH used as derivatization reagent is the chemical stability of the Lucifer Yellow moiety in aqueous solution. This property ensures the stability of the chromophore of the derivatization reagent as well as the resulting hydrazones over the time course of the analysis, even when analysis of multiple samples at one time is performed.

In one aspect, the description relates to a method for determining the total carbonylation level on a polypeptide wherein the method comprises the steps of a) contacting the polypeptide in a solution with a hydrazide dye under conditions such that the hydrazide dye can react with the carbonyl groups present on the amino acid residues of the polypeptide to form a polypeptide-dye-complex, b) removing unbound hydrazide dye from the resultant solution from step a), c) determining in the resultant solution from step b) the concentration of the hydrazide dye bound in the polypeptide-dye-complex and the concentration of the polypeptide bound in the polypeptide-dye-complex, and d) determining the total carbonylation level of the polypeptide based on the ratio of the concentration of the hydrazide dye bound in the polypeptide-dye-complex to the concentration of the polypeptide bound in the polypeptide-dye-complex.

In another aspect, the description relates to a method for determining the total carbonylation level on a polypeptide wherein the method comprises the steps of a) contacting the polypeptide in a solution with a hydrazide dye under conditions such that the hydrazide dye can react with the carbonyl groups present on the amino acid residues of the polypeptide to form a polypeptide-dye-complex, b) removing unbound hydrazide dye from the resultant solution from step a), c) applying the resultant solution from step b) to a chromatography to generate i) a chromatogram at a first wave length resulting in a first integrated peak area, and ii) a chromatogram at a second wave length resulting in a second integrated peak area, and d) determining the total carbonylation level of the polypeptide based on the ratio of the concentration of the hydrazide dye bound in the polypeptide-dye-complex to the concentration of the polypeptide bound in the polypeptide-dye-complex, each determined based on the first integrated peak area and the second integrated peak area.

In yet another aspect, the description relates to a method for determining the total carbonylation level on a polypeptide wherein the method comprises the steps of a) contacting the polypeptide in a solution with a hydrazide dye under conditions such that the hydrazide dye can react with the carbonyl groups present on the amino acid residues of the polypeptide to form a polypeptide-dye-complex, b) removing unbound hydrazide dye from the resultant solution from step a), c) applying the resultant solution from step b) to a chromatography to generate i) a chromatogram at a first wave length resulting in a first integrated peak area, and ii) a chromatogram at a second wave length resulting in a second integrated peak area, d) generating four standard curves, i) a standard curve for the hydrazide dye at the first wave length, ii) a standard curve for the hydrazide dye at the second wave length, iii) a standard curve for the polypeptide at the first wave length, and iv) a standard curve for the polypeptide at the second wave length, e) calculating the concentration of the hydrazide dye bound in the polypeptide-dye-complex and the concentration of the polypeptide bound in the polypeptide-dye-complex based on the four standard curves, the first integrated peak area and the second integrated peak area, and f) determining the total carbonylation level of the polypeptide based on the ratio of the concentration of the hydrazide dye bound in the polypeptide-dye-complex to the concentration of the polypeptide bound in the polypeptide-dye-complex.

In one embodiment, the hydrazide dye is selected from the group consisting of Cy3 hydrazide, Cy5 hydrazide, Cy5.5 hydrazide, Cy7 hydrazide, Cy7.5 hydrazide, coumarin hydrazide, iFluor™ Dye Hydrazide, HiLyte™ Fluor 647 hydrazide, Alexa Fluor® 488 hydrazide, Alexa Fluor® 568 hydrazide, Alexa Fluor® 633 hydrazide and Lucifer Yellow hydrazide. In one embodiment, the hydrazide dye is LY-CH. In one embodiment, the hydrazide dye is LY-CH dilithium salt.

In one embodiment, step a) is performed in the presence of alkali metal ions. In one embodiment, the alkali metal ions are present in a concentration of 1-100 mM. In one embodiment, the alkali metal ions are present in a concentration of 10-90 mM. In one embodiment, the alkali metal ions are present in a concentration of 20-80 mM. In one embodiment, the alkali metal ions are present in a concentration of 30-70 mM. In one embodiment, the alkali metal ions are present in a concentration of 40-60 mM. In one embodiment, the alkali metal ions are in a concentration of 45-55 mM. In one embodiment, the alkali metal ions are present in a concentration of 46-54 mM. In one embodiment, the alkali metal ions are present in a concentration of 47-53 mM. In one embodiment, the alkali metal ions are present in a concentration of 48-52 mM. In one embodiment, the alkali metal ions are present in a concentration of 49-51 mM. In one embodiment, the alkali metal ions are present in a concentration of about 50 mM. In one embodiment, the alkali metal ions are present in a concentration of 50 mM.

In one embodiment, the alkali metal ions present in step a) are selected from the group consisting of lithium ions, sodium ions and potassium ions. In one embodiment, the alkali metal ions present in step a) are lithium ions. In one embodiment, the lithium ions are present in a concentration of 1-100 mM. In one embodiment, the lithium ions are present in a concentration of 10-90 mM. In one embodiment, the lithium ions are present in a concentration of 20-80 mM. In one embodiment, the lithium ions are present in a concentration of 30-70 mM. In one embodiment, the lithium ions are present in a concentration of 40-60 mM. In one embodiment, the lithium ions are present in a concentration of 45-55 mM. In one embodiment, the lithium ions are present in a concentration of 46-54 mM. In one embodiment, the lithium ions are present in in a concentration of 47-53 mM. In one embodiment, the lithium ions are present in a concentration of 48-52 mM. In one embodiment, the lithium ions are present in a concentration of 49-51 mM. In one embodiment, the lithium ions are present in a concentration of about 50 mM. In one embodiment, the lithium ions are present in a concentration of 50 mM.

In the present description, the corrected absorbance at 428 nm is used, by subtracting the polypeptide contribution at 428 nm, to calculate the molar concentration of the carbonyl in a sample; correspondingly, the corrected absorbance at 280 nm is used, by subtracting the LY-CH contribution at 280 nm, to calculate the polypeptide concentration/amount. In comparison, other assays do not correct for the polypeptide contribution at 428 nm to the respective absorbance of the hydrazide reagent for quantifying the carbonyl content leading to an overestimation of the carbonylation content. In other words, since both the polypeptide-bound Lucifer Yellow moiety and the polypeptide component contribute to the measured absorbance peak areas at 280 nm and at 428 nm, the respective concentrations of LY-CH and the respective concentrations of the polypeptide were calculated using the standard curves generated with a LY-CH standard and with underived mAb (as the polypeptide standard). Thus, in one embodiment, a correction for the absorbance of Lucifer Yellow and a correction for the absorbance of the polypeptide are performed.

In one embodiment, the first wave length ranges from 420-440 nm. In one embodiment, the first wave length ranges from 425-435 nm. In one embodiment, the first wave length ranges from 426-430 nm. In one embodiment, the first wave length ranges from 427-428 nm. In one embodiment, the first wave length is about 428 nm. In one embodiment, the first wave length is 428 nm.

In one embodiment, the second wave length ranges from 270-290 nm. In one embodiment, the second wave length ranges from 275-285 nm. In one embodiment, the second wave length ranges from 278-282 nm. In one embodiment, the second wave length ranges from 279-281 nm. In one embodiment, the second wave length is about 280 nm. In one embodiment, the second wave length is 280 nm.

As described herein, carbonylation occurs on the amino acid residues of the polypeptide such as an antibody. In one embodiment, the amino acid residues on which carbonylation occur are selected from the group consisting of arginine, lysine, proline and threonine. In one embodiment, the carbonylation occurs on the aldehyde groups of the amino acid residues of the polypeptide. In one embodiment, the carbonylation occurs on the ketone groups of the amino acid residues of the polypeptide.

In one embodiment, the polypeptide is a homo-multimeric polypeptide. In one embodiment the polypeptide is a homo-dimer or a homo-trimer. In one embodiment, the polypeptide is a hetero-multimeric polypeptide. In one embodiment, the polypeptide is a biologically active polypeptide. In one embodiment, the polypeptide is an antibody. In one embodiment, the antibody is selected from the group consisting of a polyclonal antibody, a monoclonal antibody, a humanized antibody, a human antibody, a chimeric antibody, a multi-specific antibody, an antibody drug conjugate, a THIOMAB™ and a THIOMAB™ drug conjugate. In one embodiment, the antibody is of the class G subclass IgG1 or subclass IgG4 or variants thereof. In one embodiment, the antibody is an antibody fragment. In one embodiment, the antibody fragment is selected from Fv, Fab, Fab', Fab'-SH, diabodies, linear antibodies, single-chain antibody molecules (e.g. scFv), and multispecific antibodies formed from antibody fragments.

In one embodiment, the polypeptide and the hydrazide dye is contacted in a final molar ratio of 6,000-10,000. In one embodiment, the polypeptide and the hydrazide dye is contacted in a final molar ratio of 7,000-9,000. In one embodiment, the polypeptide and the hydrazide dye is contacted in a final molar ratio of 7,500-8,500. In one embodiment, the polypeptide and the hydrazide dye is contacted in a final molar ratio of 7,800-8,200. In one embodiment, the polypeptide and the hydrazide dye is contacted in a final molar ratio of 7,900-8,100. In one embodiment, the polypeptide and the hydrazide dye is contacted in a final molar ratio of 7,950-8,050. In one embodiment, the polypeptide and the hydrazide dye is contacted in a final molar ratio selected from the group consisting of 6,000, 7,000, 8,000, 9,000 and 10,000. In one embodiment, the polypeptide and the hydrazide dye is contacted in a final molar ratio of about 8,000. In one embodiment, the polypeptide and the hydrazide dye is contacted in a final molar ratio of 8,000. In one embodiment, the hydrazide dye is LY-CH.

In one embodiment, step a) is performed in the presence of a non-ionic surfactant. In one embodiment, the non-ionic surfactant is present in a concentration of 0.01% (w/v)-5% (w/v). In one embodiment, the non-ionic surfactant is present in a concentration of 0.1% (w/v)-5% (w/v). In one embodiment, the non-ionic surfactant is present in a concentration of 0.2% (w/v)-4% (w/v). In one embodiment, the non-ionic surfactant is present in a concentration of 0.3% (w/v)-3% (w/v). In one embodiment, the non-ionic surfactant is present in a concentration of 0.4% (w/v)-2% (w/v). In one embodiment, the non-ionic surfactant is present in a concentration of 0.5% (w/v)-1.5% (w/v). In one embodiment, the non-ionic surfactant is present in a concentration of 0.6% (w/v)-1.4% (w/v). In one embodiment, the non-ionic surfactant is present in a concentration of 0.7% (w/v)-1.3% (w/v). In one embodiment, the non-ionic surfactant is present in a concentration of 0.8% (w/v)-1.2% (w/v). In one embodiment, the non-ionic surfactant is present in a concentration of 0.9% (w/v)-1.1% (w/v). In one embodiment, the non-ionic surfactant is present in a concentration of 1% (w/v). In one embodiment, the non-ionic surfactant is present in a concentration of about 0.05% (w/v).

In one embodiment, the non-ionic surfactant is selected from the group consisting of Nonidet P-40, Poloxamer 188, Polysorbate 20, Polysorbate 80, Triton X-100, reduced Triton X-100, Tween 20 and Tween 80. In one embodiment, the non-ionic surfactant is reduced Triton X-100.

In one embodiment step a) is performed in the dark. In one embodiment, step a) is performed in a buffer which does not contain either primary or secondary amines. In one embodiment, step a) is performed in a buffer with a capacity of pH 4-7. In one embodiment, step a) is performed in a buffer which is selected from the group consisting of MES, MOPS, HEPES, and PIPES, that do not contain primary or secondary amines. In one embodiment, step a) is performed in MES buffer. In one embodiment, step a) is performed in lithium MES buffer.

In one embodiment, step a) is carried out at a pH value of 5-7. In one embodiment, step a) is carried out at a pH value of 5.5-6.5. In one embodiment, step a) is carried out at a pH value of 5.6-6.4. In one embodiment, step a) is carried out at a pH value of 5.7-6.3. In one embodiment, step a) is carried out at a pH value of 5.8-6.2. In one embodiment, step a) is carried out at a pH value of 5.9-6.1. In one embodiment, step a) is carried out at a pH value of about 5.9. In one embodiment, step a) is carried out at a pH value of about 6.0. In one embodiment, step a) is carried out at a pH value of about 6.1. In one embodiment, step a) is carried out at a pH value of 5.9. In one embodiment, step a) is carried out at a pH value of 6.0. In one embodiment, step a) is carried out at a pH value of 6.1.

In one embodiment, step a) is performed at a temperature of 35° C.-39° C. In one embodiment, step a) is performed at a temperature of 36° C.-38° C. In one embodiment, step a) is performed at a temperature of 36.5° C.-37.5° C. In one embodiment, step a) is performed at a temperature of about 37° C. In one embodiment, step a) is performed at a temperature of 37° C.

In one embodiment, step a) is performed for 1-50 h. In one embodiment, step a) is performed for 5-40 h. In one embodiment, step a) is performed for 8-30 h. In one embodiment, step a) is performed for 11-25 h. In one embodiment, step a) is performed for 12-20 h. In one embodiment, step a) is performed for 13-19 h. In one embodiment, step a) is performed for 14-18 h. In one embodiment, step a) is performed for 15-17 h. In one embodiment, step a) is performed for about 16 h. In one embodiment, step a) is performed for 16 h. In one embodiment, step a) is performed for 17-19 h. In one embodiment, step a) is performed for about 18 h. In one embodiment, step a) is performed for 18 h.

In one embodiment, the removal of the unbound hydrazide dye is performed by a method selected from the group consisting of filtration, gel filtration and dialysis. In one embodiment, the removal of the unbound hydrazide dye is performed by filtration. Any filter can be used which is capable separating the hydrazide dye from the polypeptide. In one embodiment, the filtration is carried out with filter units having a nominal molecular weight limit of 5-50 kDa. In one embodiment, the filtration is carried out with filter units having a nominal molecular weight limit of 5 kDa. In one embodiment, the filtration is carried out with filter units having a nominal molecular weight limit of 10 kDa filter. In one embodiment, the filtration is carried out with filter units having a nominal molecular weight limit of 15 kDa. In one embodiment, the filtration is carried out with filter units having a nominal molecular weight limit of 20 kDa. In one embodiment, the filtration is carried out with filter units having a nominal molecular weight limit of 25 kDa. In one embodiment, the filtration is carried out with filter units having a nominal molecular weight limit of 30 kDa. In one embodiment, the filtration is carried out with filter units having a nominal molecular weight limit of 35 kDa. In one embodiment, the filtration is carried out with filter units having a nominal molecular weight limit of 40 kDa. In one embodiment, the filtration is carried out with filter units having a nominal molecular weight limit of 45 kDa. In one embodiment, the filtration is carried out with filter units having a nominal molecular weight limit of 50 kDa. In one embodiment, the removal of the unbound hydrazide dye is performed by gel filtration. In one embodiment, the removal of the unbound hydrazide dye is performed by dialysis.

In one embodiment, filtration is carried out in the presence of 100-300 mM potassium phosphate. In one embodiment, filtration is carried out in the presence of 110-290 mM potassium phosphate. In one embodiment, filtration is carried out in the presence of 120-280 mM potassium phosphate. In one embodiment, filtration is carried out in the presence of 130-270 mM potassium phosphate. In one embodiment, filtration is carried out in the presence of 140-260 mM potassium phosphate. In one embodiment, filtration is carried out in the presence of 150-250 mM potassium phosphate. In one embodiment, filtration is carried out in the presence of 160-240 mM potassium phosphate. In one embodiment, filtration is carried out in the presence of 170-230 mM potassium phosphate. In one embodiment, filtration is carried out in the presence of 180-220 mM potassium phosphate. In one embodiment, filtration is carried out in the presence of 190-210 mM potassium phosphate. In one embodiment, filtration is carried out in the presence of 195-205 mM potassium phosphate. In one embodiment, filtration is carried out in the presence of about 200 mM potassium phosphate. In one embodiment, filtration is carried out in the presence of 200 mM potassium phosphate.

In one embodiment, filtration is carried out in the presence of 200-300 mM potassium chloride. In one embodiment, filtration is carried out in the presence of 210-290 mM potassium chloride. In one embodiment, filtration is carried out in the presence of 220-280 mM potassium chloride. In one embodiment, filtration is carried out in the presence of 230-270 mM potassium chloride. In one embodiment, filtration is carried out in the presence of 240-260 mM potassium chloride. In one embodiment, filtration is carried out in the presence of 245-255 mM potassium chloride. In one embodiment, filtration is carried out in the presence of about 250 mM potassium chloride. In one embodiment, filtration is carried out in the presence of 250 mM potassium chloride.

In one embodiment, filtration is carried out in the presence of 100-300 mM potassium phosphate and in the presence of 200-300 mM potassium chloride. In one embodiment, filtration is carried out in the presence of 200 mM potassium phosphate and in the presence of 250 mM potassium chloride.

In one embodiment, the filtration is carried out at a pH value of 5.4-7.0. In one embodiment, the filtration is carried out at a pH value of 5.5-6.9. In one embodiment, the filtration is carried out at a pH value of 5.6-6.8. In one embodiment, the filtration is carried out at a pH value of 5.7-6.7. In one embodiment, the filtration is carried out at a pH value of 5.8-6.6. In one embodiment, the filtration is carried out at a pH value of 5.9-6.5. In one embodiment, the filtration is carried out at a pH value of 6.0-6.4. In one embodiment, the filtration is carried out at a pH value of 6.1-6.3. In one embodiment, the filtration is carried out at a pH value of about 6.2. In one embodiment, the filtration is carried out at a pH value of 6.2.

In one embodiment, during the chromatography the polypeptide-dye-complex is separated from the unbound hydrazide dye such that no interference between the polypeptide-dye-complex and the unbound hydrazide dye occurs as shown in FIGS. 3A and 3B. The term "no interference" as used herein means that there is no or no relevant overlap between the baseline resolved peaks of the polypeptide-dye-complex (eluted between 10 and 22 minutes) and the baseline resolved peak of the unbound hydrazide dye (eluted at approximately 24 minutes) during chromatography.

Furthermore, size exclusion chromatography (SEC) was employed in step c) above, where the unbound LY-CH is separated from the polypeptide-dye-complex. The benefit of using SEC is that the quantitation is not affected by the variable amount of unbound LY-CH present in the samples, as demonstrated by the robustness experiment described in the Examples below. The combination of using LY-CH for the derivatization and SEC analysis for the quantitation therefore provides an improved sample preparation procedure that does not depend on exhaustively and reproducibly removing unbound hydrazide reagents for an optimal method performance.

Thus, in one embodiment, the chromatography is a size exclusion chromatography. In one embodiment, the size exclusion chromatography is carried out at an isocratic flow of 0.1-0.9 ml/min. In one embodiment, the size exclusion chromatography is carried out at an isocratic flow of 0.2-0.8 ml/min. In one embodiment, the size exclusion chromatography is carried out at an isocratic flow of 0.3-0.7 ml/min. In one embodiment, the size exclusion chromatography is carried out at an isocratic flow of 0.4-0.6 ml/min. In one embodiment, the size exclusion chromatography is carried out at an isocratic flow of about 0.5 ml/min. In one embodiment, the size exclusion chromatography is carried out at an isocratic flow of 0.5 ml/min.

In one embodiment, the size exclusion chromatography is carried out at a column temperature of 20° C.-30° C. In one embodiment, the size exclusion chromatography is carried out at a column temperature of 21° C.-29° C. In one embodiment, the size exclusion chromatography is carried out at a column temperature of 22° C.-28° C. In one embodiment, the size exclusion chromatography is carried out at a column temperature of 23° C.-27° C. In one embodiment, the size exclusion chromatography is carried out at a column temperature of 24° C.-26° C. In one embodiment, the size exclusion chromatography is carried out at a column temperature of about 25° C. In one embodiment, the size exclusion chromatography is carried out at a column temperature of 25° C.

In one embodiment, size exclusion chromatography is carried out in the presence of 100-300 mM potassium phosphate. In one embodiment, size exclusion chromatography is carried out in the presence of 110-290 mM potassium phosphate. In one embodiment, size exclusion chromatography is carried out in the presence of 120-280 mM potassium phosphate. In one embodiment, size exclusion chromatography is carried out in the presence of 130-270 mM potassium phosphate. In one embodiment, size exclusion chromatography is carried out in the presence of 140-260 mM potassium phosphate. In one embodiment, size exclusion chromatography is carried out in the presence of 150-250 mM potassium phosphate. In one embodiment, size exclusion chromatography is carried out in the presence of 160-240 mM potassium phosphate. In one embodiment, size exclusion chromatography is carried out in the presence of 170-230 mM potassium phosphate. In one embodiment, size exclusion chromatography is carried out in the presence of 180-220 mM potassium phosphate. In one embodiment, size exclusion chromatography is carried out in the presence of 190-210 mM potassium phosphate. In one embodiment, size exclusion chromatography is carried out in the presence of 195-205 mM potassium phosphate. In one embodiment, size exclusion chromatography is carried out in the presence of about 200 mM potassium phosphate. In one embodiment, size exclusion chromatography is carried out in the presence of 200 mM potassium phosphate.

In one embodiment, size exclusion chromatography is carried out in the presence of 200-300 mM potassium chloride. In one embodiment, size exclusion chromatography is carried out in the presence of 210-290 mM potassium chloride. In one embodiment, size exclusion chromatography is carried out in the presence of 220-280 mM potassium chloride. In one embodiment, size exclusion chromatography is carried out in the presence of 230-270 mM potassium chloride. In one embodiment, size exclusion chromatography is carried out in the presence of 240-260 mM potassium chloride. In one embodiment, size exclusion chromatography is carried out in the presence of 245-255 mM potassium chloride. In one embodiment, size exclusion chromatography is carried out in the presence of about 250 mM potassium chloride. In one embodiment, size exclusion chromatography is carried out in the presence of 250 mM potassium chloride.

In one embodiment, the size exclusion chromatography is carried out at a pH value of 5.4-7.0. In one embodiment, the size exclusion chromatography is carried out at a pH value of 5.5-6.9. In one embodiment, the size exclusion chromatography is carried out at a pH value of 5.6-6.8. In one embodiment, the size exclusion chromatography is carried out at a pH value of 5.7-6.7. In one embodiment, the size exclusion chromatography is carried out at a pH value of 5.8-6.6. In one embodiment, the size exclusion chromatography is carried out at a pH value of 5.9-6.5. In one embodiment, the size exclusion chromatography is carried out at a pH value of 6.0-6.4. In one embodiment, the size exclusion chromatography is carried out at a pH value of 6.1-6.3. In one embodiment, the size exclusion chromatography is carried out at a pH value of about 6.2. In one embodiment, the size exclusion chromatography is carried out at a pH value of 6.2.

In one embodiment, the four standard curves are generated by size exclusion chromatography. In one embodiment, the four standard curves are generated using the following equations:

Forth standard curve using equation 1 (polypeptide at 280 nm): $y_1 = m_1 x + b_1$ Third standard curve using equation 2 (polypeptide at 428 nm): $y_2 = m_2 x + b_2$ Second standard curve using equation 3 (Lucifer Yellow at 280 nm): $y_3 = m_3 z + b_3$ First standard curve using equation 4 (Lucifer Yellow at 428 nm): $y_4 = m_4 z + b_4$, wherein x is the concentration of the polypeptide in mg/mL, z is the molar concentration of Lucifer Yellow in μM, $m_1$ to $m_4$ and $b_1$ to $b_4$ are constants obtained from linear regression fitting.

In one embodiment, the carbonylation level of the polypeptide is calculated with as z/x (nmol/mg) by solving the two-variable (x and z) linear equations:

$$A_{280} = m_1 x + b_1 + m_3 z + b_3 \quad \text{Equation 5:}$$

$$A_{428} = m_2 x + b_2 + m_4 z + b_4 \quad \text{Equation 6:}$$

wherein z is the molar concentration (μM) of carbonyl groups and x is the protein concentration (mg/mL); $A_{280}$ is the integrated peak area of the LY-CH derived mAb species from the 280 nm absorbance as illustrated in FIG. 3A; $A_{428}$ is the integrated peak area of the LY-CH derived mAb species from the 428 nm absorbance as illustrated in FIG. 3B.

z and x can be determined by solving the linear equations 5 and 6 shown as follows.

$$x = [m_4 * A_{280} - m_3 * A_{428} - m_4 * (b_1 + b_3) + m_3 * (b_2 + b_4)] / (m_4 * m_1 - m_2 * m_3)$$

$$z = [m_2 * A_{280} - m_1 * A_{428} - m_2 * (b_1 + b_3) + m_1 * (b_2 + b_4)] / (m_2 * m_3 - m_1 * m_4)$$

Total carbonylation level is then calculated as z/x.

III. KITS

For use in the applications described herein, kits or articles of manufacture are also provided. Such kits may comprise a carrier means being compartmentalized to receive in close confinement one or more container means such as vials, tubes, and the like, each of the container means comprising one of the separate elements to be used in the method. In one embodiment, one of the container means may comprise a hydrazide dye. In one embodiment, the hydrazide dye is selected from the group consisting of Cy3 hydrazide, Cy5 hydrazide, Cy5.5 hydrazide, Cy7 hydrazide, Cy7.5 hydrazide, coumarin hydrazide, iFluor™ Dye Hydrazide, HiLyte™ Fluor 647 hydrazide, Alexa Fluor® 488 hydrazide, Alexa Fluor® 568 hydrazide, Alexa Fluor® 633 hydrazide and LY-CH. In one embodiment, the hydrazide dye is LY-CH. In one embodiment, the hydrazide dye is LY-CH dilithium salt. In one embodiment, one of the container means comprises a buffer. In one embodiment, one of the container means comprises a buffer which comprises lithium ions. In one embodiment, the buffer does not contain either primary or secondary amines. In one embodiment, the buffer has a capacity of pH 4-7. In one embodiment, the buffer which is selected from the group consisting of MES, MOPS, HEPES, and PIPES, that do not contain primary or secondary amines. In one embodiment, the buffer is lithium MES buffer. In one embodiment, the buffer is lithium MES buffer at a pH value of 6.0. In one embodiment, the buffer is lithium MES buffer at a pH value of 6.1.

In one embodiment, one of the container means comprises a non-ionic surfactant. In one embodiment, the non-ionic surfactant is selected from the group consisting of Nonidet P-40, octyl-beta-glucoside, Poloxamer 188, Polysorbate 20, Polysorbate 80, Triton X-100, reduced Triton X-100, Tween 20 and Tween 80. In one embodiment, the non-ionic surfactant is reduced Triton X-100.

In one embodiment, one of the container means comprises a standard for the polypeptide and one of the container means comprises a standard for hydrazide dye. In one embodiment, one of the container means comprises a filter unit. In one embodiment, the filter unit is a 30 kDa filter unit. In one embodiment, one of the container means comprises potassium phosphate. In one embodiment, one of the container means comprises potassium chloride.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a non-therapeutic application, and may also indicate directions for in vitro use, such as those described above. Other optional components in the kit include one or more buffers (e.g., derivatization buffer, block buffer, wash buffer, substrate buffer, etc.), other reagents such as substrate (e.g., chromogen) which is chemically altered by an enzymatic label, epitope retrieval solution, control samples (positive and/or negative controls), control slide(s) etc.

IV. SPECIFIC EMBODIMENTS

1. A method for determining the total carbonylation level on a polypeptide wherein the method comprises the steps of
   a) Contacting the polypeptide in a solution with a hydrazide dye under conditions such that the hydrazide dye can react with the carbonyl groups present on the amino acid residues of the polypeptide to form a polypeptide-dye-complex,
   b) Removing unbound hydrazide dye from the resultant solution from step a),
   c) Determining in the resultant solution from step b) the concentration of the hydrazide dye bound in the polypeptide-dye-complex and the concentration of the polypeptide bound in the polypeptide-dye-complex, and
   d) Determining the total carbonylation level of the polypeptide based on the ratio of the concentration of the hydrazide dye bound in the polypeptide-dye-complex to the concentration of the polypeptide bound in the polypeptide-dye-complex.

2. A method for determining the total carbonylation level on a polypeptide wherein the method comprises the steps of
   a) Contacting the polypeptide in a solution with a hydrazide dye under conditions such that the hydrazide dye can react with the carbonyl groups present on the amino acid residues of the polypeptide to form a polypeptide-dye-complex,
   b) Removing unbound hydrazide dye from the resultant solution from step a),
   c) Applying the resultant solution from step b) to a chromatography to generate i) a chromatogram at a first wave length resulting in a first integrated peak area, and ii) a chromatogram at a second wave length resulting in a second integrated peak area, and
   d) Determining the total carbonylation level of the polypeptide based on the ratio of the concentration of the hydrazide dye bound in the polypeptide-dye-complex to the concentration of the polypeptide bound in the polypeptide-dye-complex, each determined based on the first integrated peak area and the second integrated peak area.

3. A method for determining the total carbonylation level on a polypeptide wherein the method comprises the steps of
   a) Contacting the polypeptide in a solution with a hydrazide dye under conditions such that the hydrazide dye can react with the carbonyl groups present on the amino acid residues of the polypeptide to form a polypeptide-dye-complex,
   b) Removing unbound hydrazide dye from the resultant solution from step a),
   c) Applying the resultant solution from step b) to a chromatography to generate i) a chromatogram at a first wave length resulting in a first integrated peak area, and ii) a chromatogram at a second wave length resulting in a second integrated peak area,
   d) Generating four standard curves, i) a standard curve for the hydrazide dye at the first wave length, ii) a standard curve for the hydrazide dye at the second wave length, iii) a standard curve for the polypeptide at the first wave length, and iv) a standard curve for the polypeptide at the second wave length,
   e) Calculating the concentration of the hydrazide dye bound in the polypeptide-dye-complex and the concentration of the polypeptide bound in the polypeptide-dye-complex based on the four standard curves, the first integrated peak area and the second integrated peak area, and
   f) Determining the total carbonylation level of the polypeptide based on the ratio of the concentration of the hydrazide dye bound in the polypeptide-dye-complex to the concentration of the polypeptide bound in the polypeptide-dye-complex.

4. The method according to any one of the previous embodiments, wherein the hydrazide dye is selected from the group consisting of Cy3 hydrazide, Cy5 hydrazide, Cy5.5 hydrazide, Cy7 hydrazide, Cy7.5 hydrazide, coumarin hydrazide, iFluor™ Dye Hydrazide, HiLyte™ Fluor 647 hydrazide, Alexa Fluor® 488 hydrazide, Alexa Fluor® 568 hydrazide, Alexa Fluor® 633 hydrazide and LY-CH.

5. The method according to any one of the previous embodiments, wherein the hydrazide dye is LY-CH.

6. The method according to any one of the previous embodiments, wherein step a) is performed in the presence of alkali metal ions.

7. The method according to embodiment 6, wherein the alkali metal ions are present in a concentration of 1-100 mM.

8. The method according to embodiment 6, wherein the alkali metal ions are present in a concentration of 50 mM.

9. The method according to any one of embodiment 6-8, wherein the alkali metal ions are selected from the group consisting of lithium ions, sodium ions and potassium ions.

10. The method according to any one of embodiment 6-8, wherein the alkali metal ions are lithium ions.

11. The method according to any one of the previous embodiments, wherein step a) is performed in lithium MES buffer.

12. The method according to any one of the previous embodiments, wherein the reaction in step a) is a derivatization.

13. The method according to any one of the previous embodiments, wherein the first wave length is in the range of 426 nm-430 nm.

14. The method according to any one of the previous embodiments, wherein the first wave length is 428 nm.

15. The method according to any one of the previous embodiments, wherein the second wave length is in the range of 278 nm-282 nm.

16. The method according to any one of the previous embodiments, wherein the second wave length is 280 nm.

17. The method according to any one of the previous embodiments, wherein the amino acid residues are selected from the group consisting of arginine, lysine, proline and threonine.

18. The method according to any one of the previous embodiments, wherein the polypeptide is an antibody.

19. The method according to embodiment 18, wherein the antibody is a polyclonal antibody, a monoclonal antibody, a humanized antibody, a human antibody, a chimeric antibody, a multi-specific antibody, an antibody fragment, an antibody drug conjugate, a THIOMAB™ or a THIOMAB™ drug conjugate.

20. The method according to any one of the previous embodiments, wherein the polypeptide and the hydrazide dye is contacted in step a) in a final molar ratio of 6,000-10,000.

21. The method according to any one of the previous embodiments, wherein the polypeptide and the hydrazide dye is contacted in step a) in a final molar ratio of 8,000.

22. The method according to any one of the previous embodiments, wherein step a) is performed in the presence of a non-ionic surfactant.

23. The method according to embodiment 22, wherein the non-ionic surfactant is selected from the group consisting of Nonidet P-40, Poloxamer 188, Polysorbate 20, Polysorbate 80, Triton X-100, reduced Triton X-100, Tween 20 and Tween 80.

24. The method according to embodiment 22, wherein the non-ionic surfactant is reduced Triton X-100.

25. The method according to any one of the embodiments 22-24, wherein the non-ionic surfactant is present in a concentration of 0.01% (w/v)-5% (w/v).

26. The method according to any one of the embodiments 22-24, wherein the non-ionic surfactant is present in a concentration of 0.05% (w/v).

27. The method according to any one of the embodiments 22-24, wherein the non-ionic surfactant is present in a concentration of 1% (w/v).

28. The method according to any one of the previous embodiments, wherein step a) is performed in the dark.

29. The method according to any one of the previous embodiments, wherein step a) is carried out at a pH value of 5-7.

30. The method according to any one of the previous embodiments, wherein step a) is carried out at a pH value of 6.0.

31. The method according to any one of the previous embodiments, wherein step a) is carried out at a pH value of 6.1.

32. The method according to any one of the previous embodiments, wherein step a) is performed at a temperature of 35° C.-39° C.

33. The method according to any one of the previous embodiments, wherein step a) is performed at a temperature of 37° C.

34. The method according to any one of the previous embodiments, wherein step a) is performed for 10-20 h.

35. The method according to any one of the previous embodiments, wherein step a) is performed for 16 h.

36. The method according to any one of the previous embodiments, wherein step a) is performed for 18 h.

37. The method according to any one of the previous embodiments, wherein the removal of the unbound hydrazide dye in step b) is performed by a method selected from the group consisting of filtration, gel filtration and dialysis.

38. The method according to any one of the previous embodiments, wherein the removal of the unbound hydrazide dye is performed by filtration.

39. The method according to embodiment 35, wherein the filtration is carried out with filter units having a nominal molecular weight limit of 5-50 kDa.

40. The method according to any one of the embodiments 35, wherein the filtration is carried out with filter units having a nominal molecular weight limit of 30 kDa.

41. The method according to any one of the embodiments 35-37, wherein filtration is carried out in the presence of 100-300 mM potassium phosphate.

42. The method according to any one of the embodiments 35-38, wherein filtration is carried out in the presence of 200 mM potassium phosphate.

43. The method according to any one of the embodiments 35-39, wherein filtration is carried out in the presence of 200-300 mM potassium chloride.

44. The method according to any one of the embodiments 35-40, wherein filtration is carried out in the presence of 250 mM potassium chloride.

45. The method according to any one of the embodiments 35-41, wherein the filtration is carried out at a pH value of 6-7.

46. The method according to any one of the embodiments 35-42, wherein filtration is carried out at a pH value of 6.2

47. The method according to any one of embodiments 2-43, wherein during the chromatography the polypeptide-dye-complex is separated from the unbound hydrazide dye such that no interference between the polypeptide-dye-complex and the unbound hydrazide dye occurs.

48. The method according to any one of embodiments 2-44, wherein the chromatography is a size exclusion chromatography.

49. The method according to embodiment 45, wherein size exclusion chromatography is carried out at an isocratic flow of 0.2-0.8 ml/min.

50. The method according to any one of embodiments 45, wherein size exclusion chromatography is carried out at an isocratic flow of 0.5 ml/min.

51. The method according to any one of embodiments 45-47, wherein size exclusion chromatography is carried out at a column temperature of 20° C.-30° C.

52. The method according to any one of embodiments 45-48, wherein size exclusion chromatography is carried out at a column temperature of 25° C.

53. The method according to any one of embodiments 45-49, wherein size exclusion chromatography is carried out in the presence of 100-300 mM potassium phosphate.

54. The method according to any one of embodiments 45-50, wherein size exclusion chromatography is carried out in the presence of 200 mM potassium phosphate 55. The method according to any one of embodiments 45-51, wherein size exclusion chromatography is carried out in the presence of 200-300 mM potassium chloride.

56. The method according to any one of embodiments 45-52, wherein size exclusion chromatography is carried out in the presence of 250 mM potassium chloride.

57. The method according to any one of embodiments 45-53, wherein size exclusion chromatography is carried out at a pH value of 6-7.

58. The method according to any one of embodiments 45-54, wherein size exclusion chromatography is carried out at a pH value of 6.2.

59. The method according to any one of embodiments 3-55, wherein the four standard curves are generated by size exclusion chromatography.

60. The method according to any one of embodiments 3 to 56, wherein the four standard curves are generated using the following equations:

Forth standard curve using equation 1 (polypeptide at 280 nm): $y_1 = m_1 x + b_1$ Third standard curve using equation 2 (polypeptide at 428 nm): $y_2 = m_2 x + b_2$ Second standard curve using equation 3 (Lucifer Yellow at 280 nm): $y_3 = m_3 z + b_3$ First standard curve using equation 4 (Lucifer Yellow at 428 nm): $y_4 = m_4 z + b_4$, wherein x is the concentration of the polypeptide in mg/mL, z is the molar concentration of Lucifer Yellow in μM, $m_1$ to $m_4$ and $b_1$ to $b_4$ are constants obtained from linear regression fitting.

61. The method according to any one of embodiments 3 to 57, wherein the carbonylation level of the polypeptide is calculated with as z/x (nmol/mg) by solving the two-variable (x and z) linear equations:

$$A_{280} = m_1 x + b_1 + m_3 z + b_3 \quad \text{Equation 5:}$$

$$A_{428} = m_2 x + b_2 + m_4 z + b_4 \quad \text{Equation 6:}$$

wherein z is the molar concentration (μM) of carbonyl groups and x is the protein concentration (mg/mL); $A_{280}$ is the integrated peak area of the LY-CH derived mAb species from the 280 nm absorbance as illustrated in FIG. 3A; $A_{428}$ is the integrated peak area of the LY-CH derived mAb species from the 428 nm absorbance as illustrated in FIG. 3B.

z and x can be determined by solving the linear equations 5 and 6 shown as follows.

$$x = [m_4 * A_{280} - m_3 * A_{428} - m_4 * (b_1 + b_3) + m_3 * (b_2 + b_4)] / (m_4 * m_1 - m_2 * m_3)$$

$$z = [m_2 * A_{280} - m_1 * A_{428} - m_2 * (b_1 + b_3) + m_1 * (b_2 + b_4)] / (m_2 * m_3 - m_1 * m_4)$$

Total carbonylation level is then calculated as z/x.

62. A kit for carrying out the method according to any one of the previous embodiments, wherein the kit comprises hydrazide dye and a buffer.

63. The kit according to embodiment 59, wherein the hydrazide dye is selected from the group consisting of Cy3 hydrazide, Cy5 hydrazide, Cy5.5 hydrazide, Cy7 hydrazide, Cy7.5 hydrazide, coumarin hydrazide, iFluor™ Dye Hydrazide, HiLyte™ Fluor 647 hydrazide, Alexa Fluor® 488 hydrazide, Alexa Fluor® 568 hydrazide, Alexa Fluor® 633 hydrazide and LY-CH.

64. The kit according to embodiment 59, wherein the hydrazide dye is LY-CH.

65. The kit according to embodiment 59-61, wherein the buffer is lithium MES buffer.

66. The kit according to embodiment 59-62, wherein the kit further comprises a non-ionic surfactant.

67. The kit according to embodiment 63, wherein the non-ionic surfactant is selected from the group consisting of Nonidet P-40, Poloxamer 188, Polysorbate 20, Polysorbate 80, Triton X-100, reduced Triton X-100, Tween 20 and Tween 80.

68. The kit according to embodiment 63, wherein the non-ionic surfactant is reduced Triton X-100.

69. The kit according to embodiment 59-65, wherein the kit further comprises a standard for the polypeptide and a standard for hydrazide dye.

V. EXAMPLES

The following are examples of methods according to the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Materials

All mAbs used in the present description were manufactured at Genentech (South San Francisco, Calif.). LY-CH dilithium salt, ferrous sulfate, hydrogen peroxide solution (30% in $H_2O$, w/w), methionine (Met), ethylenediaminetetraacetic acid (EDTA), sodium succinate, succinic acid, potassium phosphate (dibasic and monobasic), potassium chloride, sodium acetate, acetic acid, sodium hydroxide solution (1M in $H_2O$), 2-(N-morpholino)ethanesulfonic acid (MES), lithium hydroxide, reduced Triton X-100, and Polysorbate 20 were purchased from Sigma-Aldrich (St. Louis, Mo., USA). TSK G3000 SWXL (7.8×300 mm) size exclusion column was purchased from Tosoh Bioscience (King of Prussia, Pa., USA). OxiSelect™ protein carbonyl assay kit was purchased from Cell Biolabs (San Diego, Calif., USA). PNGase F (glycerol free) was purchased from New England Biolabs (Ipswich, Mass., USA).

Example 1

Preparation of the Oxidized mAb Samples and Derivatization of the mAb Samples with LY-CH The oxidized mAb samples, referred to as the oxi-standard mAb or the oxi-standard mAb (II), were generated for the method described herein using the Fenton's reaction. Therefore, antibody samples were mixed with $FeSO_4$ and hydrogen peroxide to 5 mg/mL, 2 mM, and 10 mM, respectively, of the final concentrations, in a 50 mM sodium succinate buffer, pH 6.5. The reaction mixture was incubated at room temperature for 2 h and subsequently stopped by adding excess amount of methionine and EDTA.

The derivatization was carried out in a derivatization buffer (50 mM lithium MES buffer, 1% Triton X-100, pH 6.0), which was prepared by titrating the MES solution with 1M lithium hydroxide solution to pH 6.0. The mAb samples were first buffer exchanged into the derivatization buffer using Amicon Ultra-15 30 KDa filter units (Millipore, Billerica, Mass., USA). Subsequently, the mAb samples (0.2 mg/mL final concentration) were mixed with LY-CH (with a final LY-CH-to-mAb molar ratio of 8,000) and the reduced Triton X-100 (1% weight/volume final concentration) in the derivatization buffer. The derivatization was carried out in the dark at 37° C. for 16 h. After the derivatization, an aliquot of 500 μL of the derivatized sample was buffer exchanged three times into 200 mM potassium phosphate, 250 mM potassium chloride, pH 6.2 using the 15 mL Amicon Ultra-15 30 kDa filter units.

The derivatization was carried out in a derivatization buffer (50 mM lithium MES buffer, 0.05% Triton X-100, pH 6.0), which was prepared by titrating the MES solution with 1M lithium hydroxide solution to pH 6.0. The mAb samples were first buffer exchanged into the derivatization buffer using Amicon Ultra-15 30 KDa filter units (Millipore, Billerica, Mass., USA). Subsequently, the mAb samples (0.5 mg/mL final concentration) were mixed with LY-CH (with a final LY-CH-to-mAb molar ratio of 8,000) and the reduced Triton X-100 (0.05% weight/volume final concentration) in the derivatization buffer. The derivatization was carried out in the dark at 37° C. for 18 h. After the derivatization, an aliquot of 500 μL of the derivatized sample was buffer exchanged three times into 200 mM potassium phosphate, 250 mM potassium chloride, pH 6.2 using the 15 mL Amicon Ultra-15 30 kDa filter units.

Example 2

Determination of the Protein Carbonyl Levels of mAbs

Figure 2B:
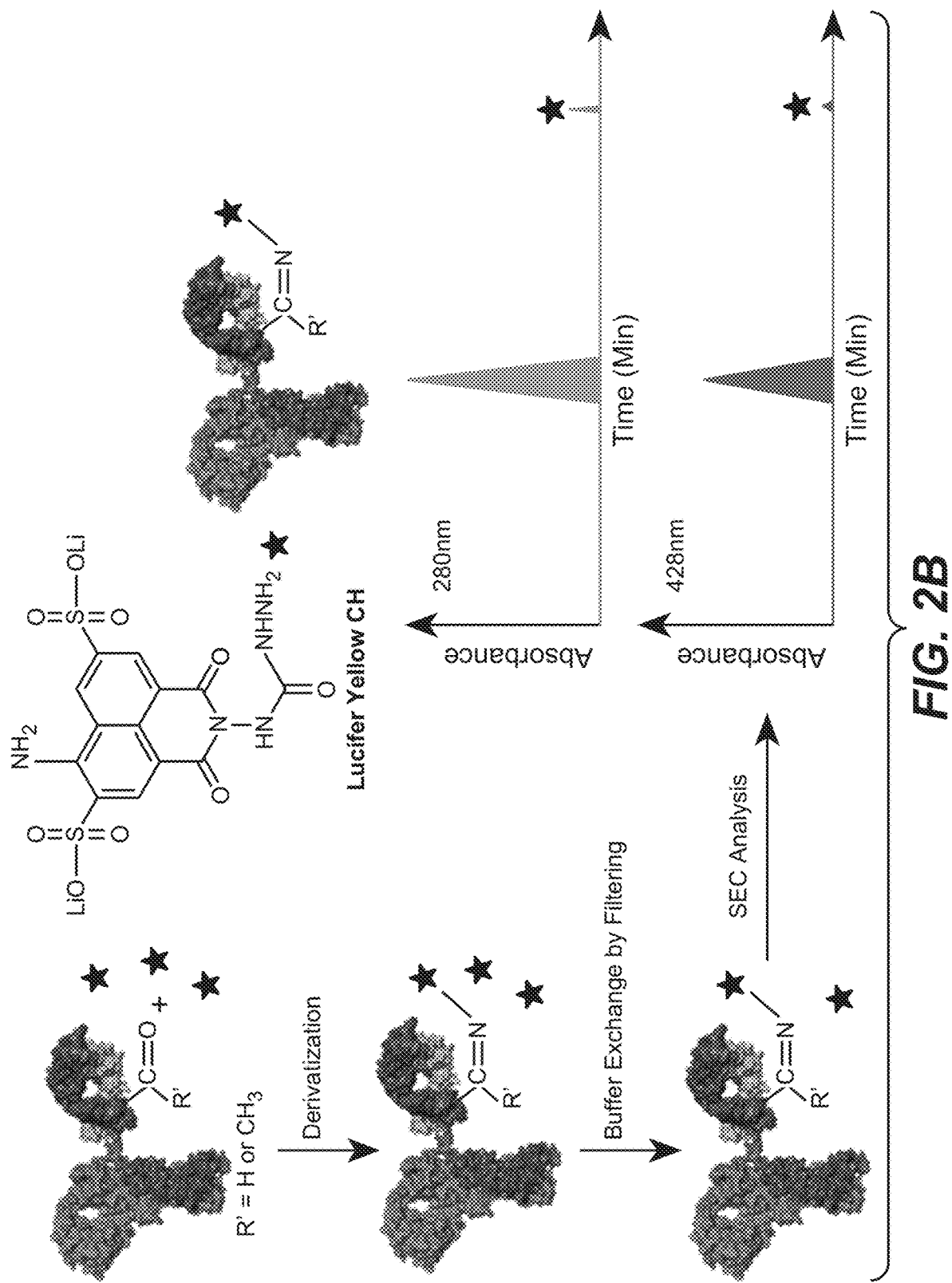
FIG. 2B shows the workflow of CALY.

The overall workflow of CALY is illustrated in FIG. 2B. The mAb samples were analyzed by size exclusion chromatography using a TSK G3000 SWXL (7.8×300 mm) size exclusion column with an isocratic flow of 0.5 ml/min generated by an Agilent HPLC system. The mobile phase contained 200 mM potassium phosphate, 250 mM potassium chloride at pH 6.2. The column temperature was controlled at 25° C. and the autosampler temperature was controlled at 8° C. For each sample, 254 of the mAb material (approximately 25 µg) was injected for the analysis. The effluent was monitored by the UV absorbance at both 280 nm and 428 nm.

After the derivatization and the buffer exchange, the mAb samples were analyzed by size exclusion chromatography, where residual LY-CH in the sample was separated from the derived mAb. Quantification of the carbonylation level was based on the UV 280 nm and 428 nm absorbance peak areas of the derived mAb (eluted at approximately between 10 and 22 minutes) on the size exclusion chromatogram. Since both the protein-bound Lucifer Yellow moiety and the protein component contribute to the measured UV 280 and 428 nm absorbance peak areas, the respective concentrations of the Lucifer Yellow moiety and the protein were calculated using the standard curves of LY-CH standard and the underived mAb (as the protein standard).

The mAb standard curves were prepared by size exclusion chromatography analysis of the corresponding underived mAb sample with 254 injections at various protein concentrations (0.25, 0.5, 1, 2, and 3 mg/mL). The LY-CH standard curves were prepared similarly by injecting 25 µL of LY-CH standards at various molar concentrations (1, 5, 10, 15, and 20 µM). Four linear equations were generated by linear regression fit of the resulting UV absorbance peak areas against the concentrations for the mAb and LY-CH standard, respectively. In these equations, x is mAb protein concentration (mg/mL); z is LY-CH molar concentration (µM); $m_1$ to $m_4$ and $b_1$ to $b_4$ are the constants obtained from the linear regression fitting.

(UV 280 nm response of mAb): $y_1 = m_1 x + b_1$      Equation 1

(UV 428 nm response of mAb): $y_2 = m_2 x + b_2$      Equation 2

(UV 280 nm response of LY-CH): $y_3 = m_3 z + b_3$      Equation 3

(UV 428 nm response of LY-CH): $y_4 = m_4 z + b_4$      Equation 4

Figure 4A:
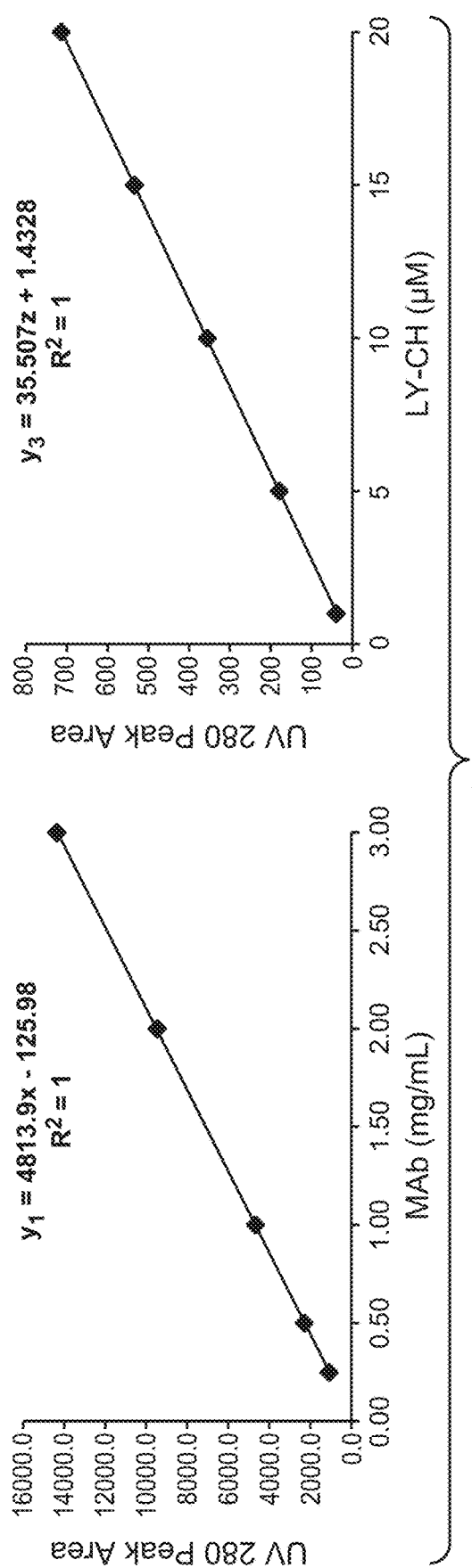
FIG. 4A shows the standard curves for the polypeptide and LY-CH at 280 nm. After linear regression fit of the standard curves, m1=4813.9; b1=−125.98; m3=35.507; b3=1.4328.
Figure 4B:
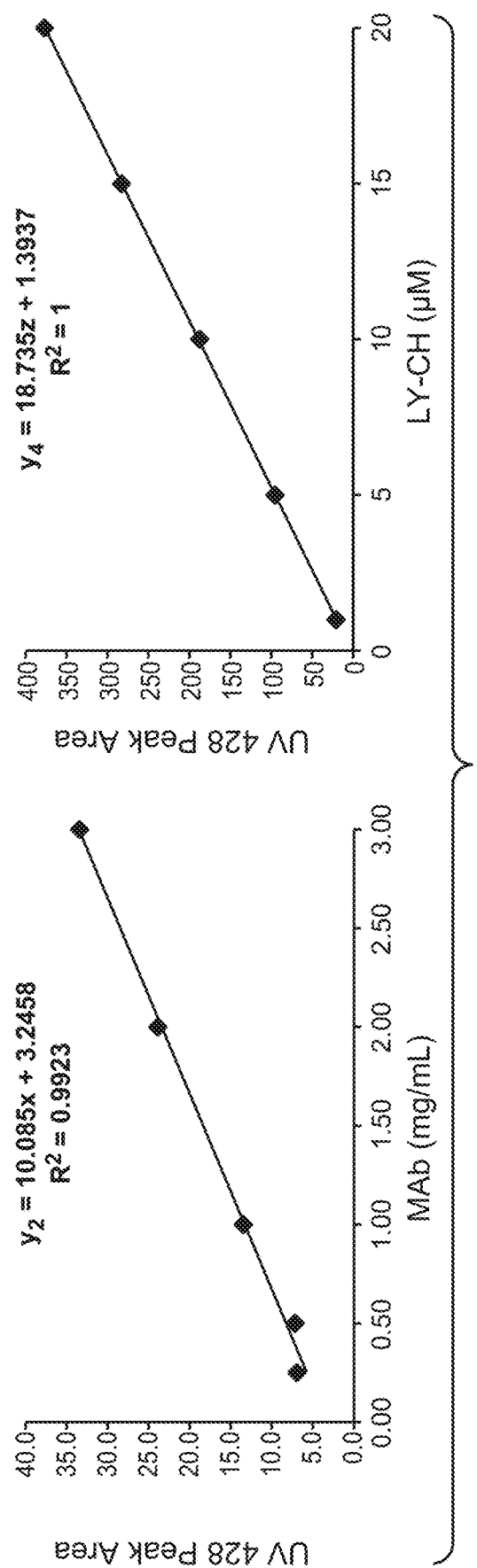
FIG. 4B shows the standard curves for the polypeptide and LY-CH at 428 nm. After linear regression fit of the standard curves, m2=10.085; b2=3.2458; m4=18.735; b4=1.3937.

As shown in FIG. 4A and 4B, after linear regression fit of the standard curves, m1=4813.9; b1=−125.98; m2=10.085; b2=3.2458; m3=35.507; b3=1.4328; m4=18.735; b4=1.3937.

The carbonylation level of the mAb sample was then calculated as z/x (nmol/mg) by solving the two-variable (x and z) linear equations 5 and 6, where x is the molar concentration (µM) of carbonyl groups and z is the protein concentration (mg/mL).

$A_{280} = m_1 x + b_1 + m_3 z + b_3$      Equation 5

$A_{428} = m_2 x + b_2 + m_4 z + b_4$      Equation 6

To illustrate the quantitation process, a typical size exclusion chromatogram of the derived oxi-standard mAb is shown in FIG. 3A and 3B. The four standard curves from the underived oxi-standard mAb and the LY-CH are shown in FIG. 4A and 4B, which demonstrated the linear response between the absorbance peak areas and respective mAb and LY-CH concentrations. The coefficient of determination ($R^2$) from the linear regression fitting of the data were greater than 0.99. The total carbonylation level for each derivatization condition was then calculated based on the integrated peak areas from the derived oxi-standard mAb and the four equations from the standard curves. As an example, the A280 and A428 values were determined as follows. The peak area of 4347.7, A280, is a result of the absorbance contributions of the mAb and the LY-CH at 280 nm and was determined by integrating the area under the curve from approximately 10.1 min to 22.2 min in the SEC profile. Accordingly, the peak area of 224.0, A428, was determined by integrating the area under the curve from approximately 10.1 min to 22.2 min in the SEC profile with the absorbance at 428 nm. In connection with the above Equations 5 and 6 this resulted in the following two equations:

$4347.7 = 4813.9 \ast x - 125.98 + 35.507 \ast z + 1.4328$      i)

$224.0 = 10.085 \ast x + 3.2458 + 18.735 \ast z + 1.3937$      ii)

The two variables x and z were then determined by solving the two linear equations i) and ii), with x=0.846 mg/mL mAb and z=11.253 µM LY-CH resulting in a carbonylation level of 13.3 nmol/mg.

Example 3

Optimization of the Derivatization Condition

Identifying the Optimal Buffer System and pH Value

To establish an optimal derivatization condition for CALY, the oxi-standard mAb samples as described in Example 1 above were used as a test sample to optimize the derivatization buffer, the LY-CH-to-mAb molar ratio, and the derivatization time. To identify an optimal buffer that allows the use of LY-CH as the derivatization reagent, first different buffer pH values for the derivatization reaction were considered. At and below pH 5.0, some degree of sample precipitation during the derivatization reaction was observed. To avoid the sample precipitation, pH 6.0 as the derivatization pH was selected based on the consideration that no precipitation was observed at above pH 5.0 and that at pH 7.0 and higher the derivatization reaction becomes significantly slower. Correspondingly, the MES with a pKa of 6.13 was selected as the buffer system. The buffer was prepared by titrating 50 mM MES solution to pH 6.0 using lithium hydroxide. The use of lithium hydroxide for the buffer preparation was based on the consideration that the lithium salt of LY-CH has higher solubility than the sodium and potassium salts. The resulting higher solubility of LY-CH with lithium ions in the buffer allows the use of higher LY-CH-to-mAb molar ratio for the derivatization reaction and allows an easier removal of the residual LY-CH reagent after the derivatization. Finally, another factor considered is that oxidized protein samples tend to have higher aggregation propensity, which can potentially cause sample precipitation during the derivatization reaction. To address that concern, reduced Triton X-100 as surfactant was added to a final concentration of 0.05% or 1% (weight to volume) in the derivatization buffer. Reduced Triton X-100 does not have any significant absorbance at 280 and 428 nm. With the final optimized buffer system, no sample precipitation was observed in all the subsequent analyses.

Optimization of LY-CH to Sample Molar Ratio and Derivatization Time

Figure 5:
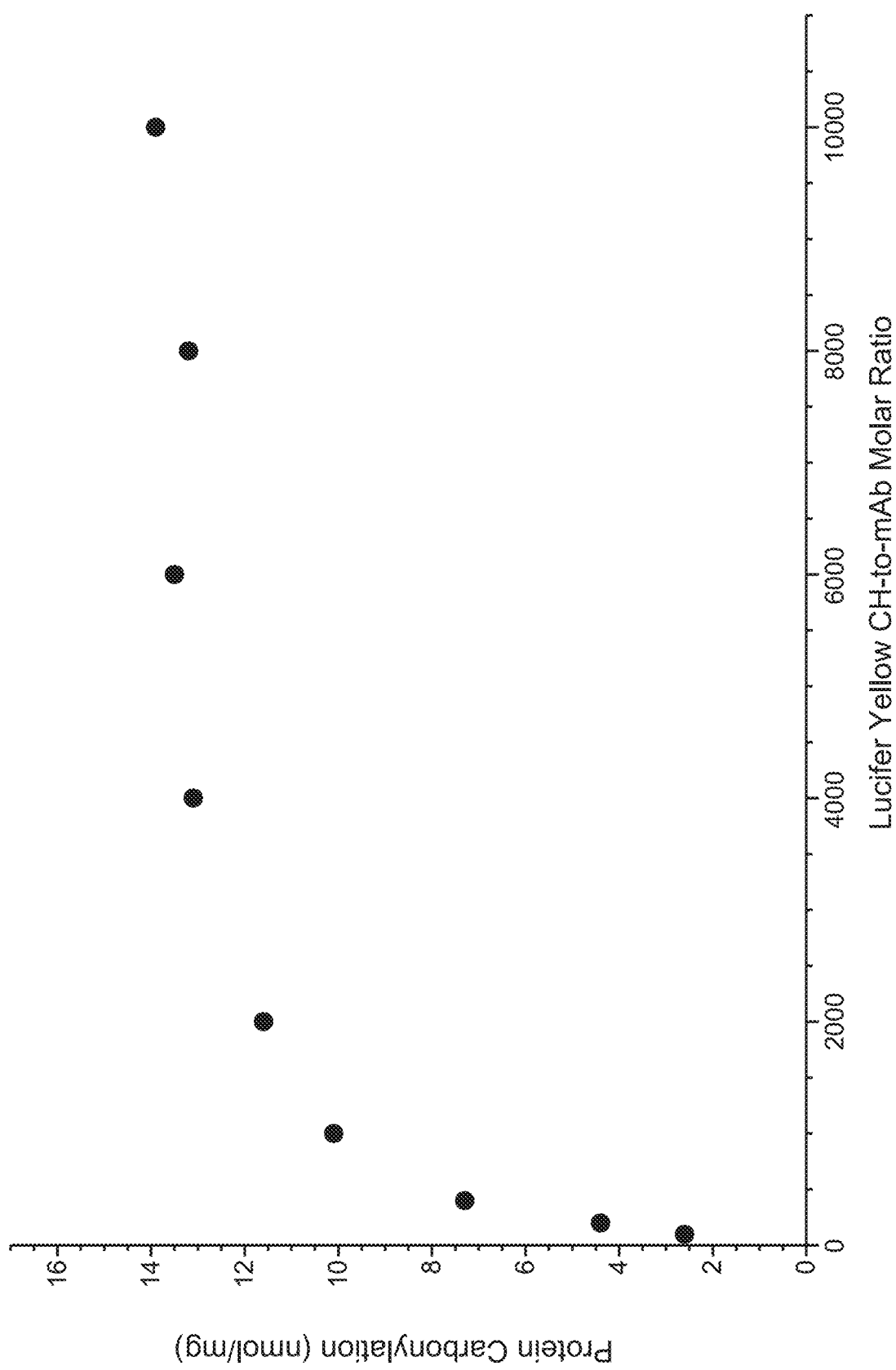
FIG. 5 shows the optimization of the derivatization reaction condition on LY-CH-to-mAb molar ratio with the reaction time of 18 h.
Figure 6:
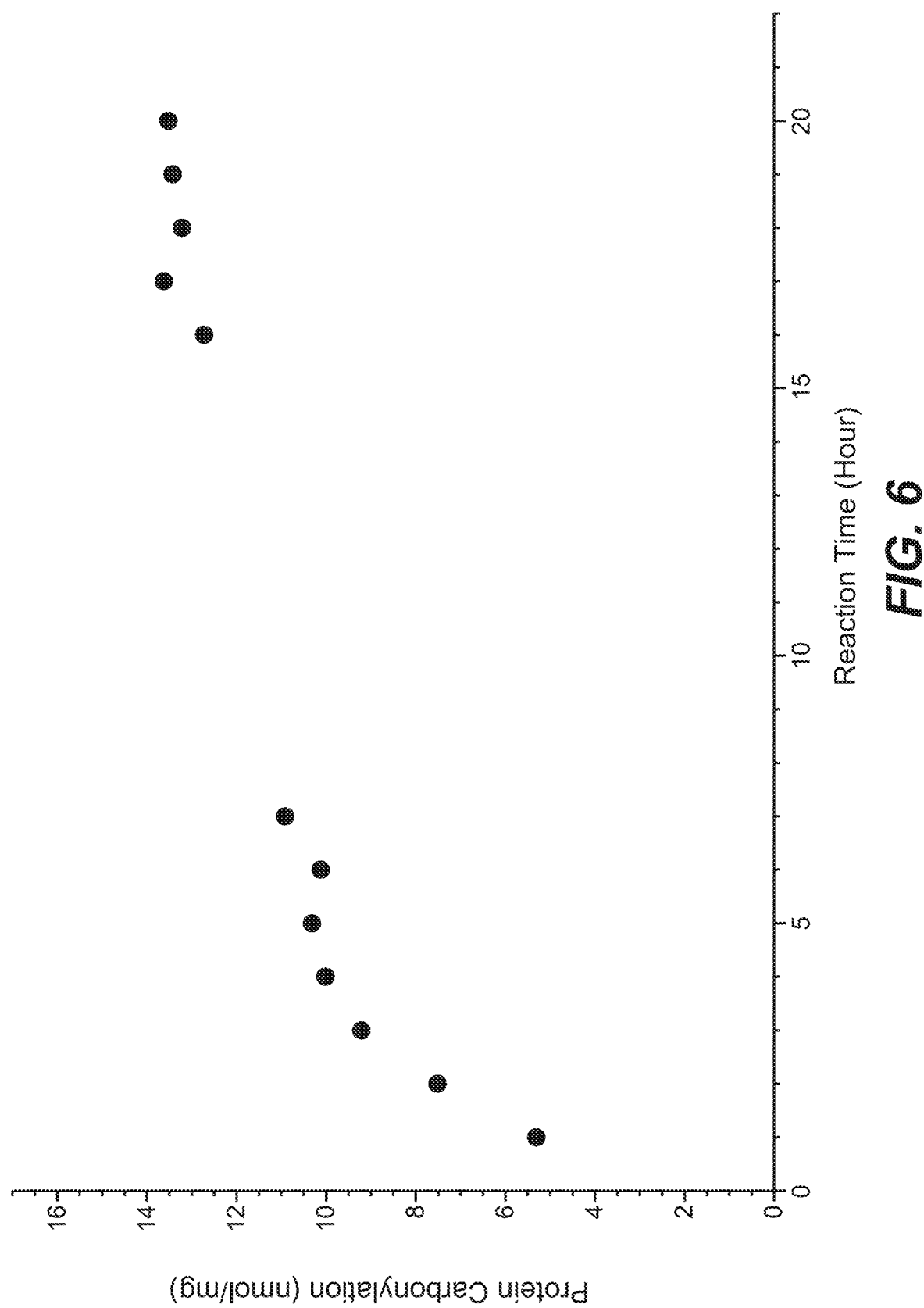
FIG. 6 shows the optimization of the derivatization reaction condition on the reaction time with the LY CH-to-mAb molar ratio of 8000:1.

The LY-CH to sample molar ratio and the derivatization time were optimized by quantifying the level of total carbonylation of the oxi-standard mAb at various derivatization conditions. First, the LY-CH to sample molar ratio was optimized by evaluating the extent of derivatization with various molar ratios at 50, 500, 1000, 1500, 2000, 4000, 6000, 8000, and 10,000. All other derivatization conditions, such as the final oxi-standard mAb concentration (0.2 mg/mL) in the reaction mixture, reaction temperature (37° C.), and reaction time (18 hours), were unchanged at the target condition. The corresponding carbonylation levels from the various molar ratios (FIG. 5) showed that the derivatization reaction has reached a plateau at the molar ratio of 8000, beyond which no significant increase of carbonylation level is observed. Therefore, the LY-CH to sample molar ratio of 8000 was selected as the final condition for the derivatization reaction. Similarly, the reaction time was optimized by varying the incubation time while keeping the molar ratio at 8000 and all other derivatization conditions unchanged at the target condition. The resulting total carbonylation levels (FIG. 6) showed that the derivatization reaction reached a plateau at 18 hours. Therefore 18 hours as the final reaction time for the derivatization reaction was selected.

Example 4

Assessment of CALY

Robustness Assessment

The robustness of CALY was assessed by applying minor changes to one method condition/parameter at a time with other method conditions unchanged, and subsequently evaluating the effect of these minor changes on the total carbonylation result of the oxi-standard mAb. Specifically, the effect of the derivatization reaction conditions, the sample handling and analysis process after the derivatization, and the stability of the derivatized sample during the SEC analysis for the assessment were investigated. For the derivatization reaction conditions, the total carbonylation levels of the oxi-standard mAb from different mAb protein concentrations (0.45, 0.50, and 0.55 mg/mL), different LY-to-mAb molar ratios (7000:1, 8000:1, and 9000:1), and different pH values of the derivatization buffer (5.9, 6.0, and 6.1) were compared. As shown in FIG. 7A to 7B, very little variation in the carbonylation levels was observed for the reaction protein concentrations, or the LY-CH-to-mAb molar ratios. From the buffer pH robustness data, the total carbonylation level from pH 6.1 was slightly lower than those from pH 5.9 and 6.0 (FIG. 7C), which is likely due to a slightly slower reaction rate at pH 6.1 and suggests that a rigorous control of the derivatization buffer pH may be necessary for the optimal method robustness.

For the sample handling process, it is worth mentioning that, after the derivatization, each round of buffer exchange by filtering is equivalent of reducing the amount of residual LY-CH present in the sample by a factor of approximately 50. The effect of using two, three, and four rounds of buffer exchange was investigated to understand whether various amounts of residual LY-CH in the sample affect the carbonylation result. As shown in FIG. 7D, no significant difference was observed in the results with two, three, or four rounds of buffer exchange, which demonstrates that the presence of various amounts of residual LY-CH in the derivatized sample has very little effect on the results. For the size exclusion analysis, we tested various injection volumes (from 20 µL to 30 µL) for the derivatized and buffer-exchanged oxi-standard mAb. The corresponding carbonylation levels are shown in FIG. 7E, which demonstrated that the method is robust against minor variation in injection volume/amount.

Figure 8:
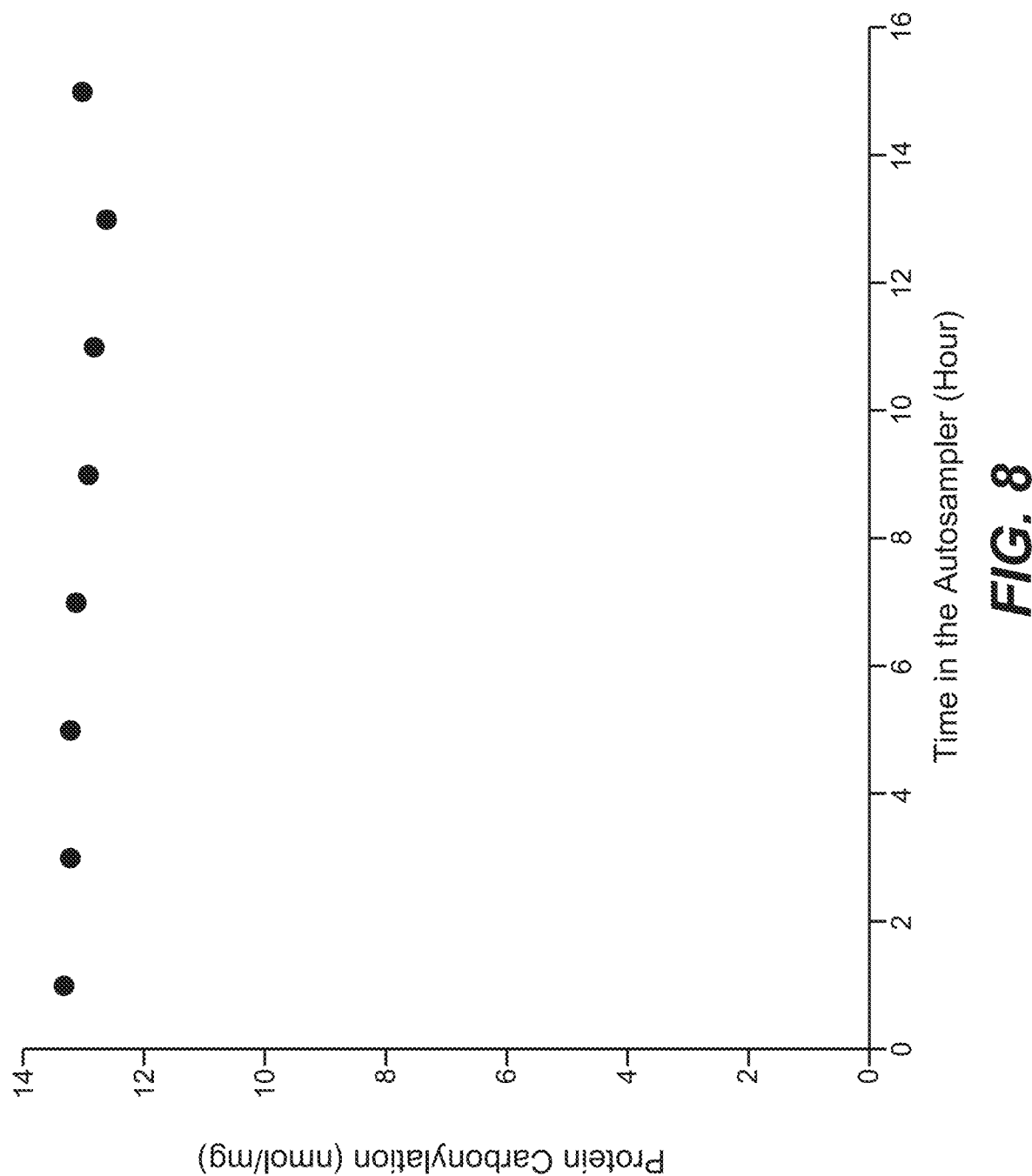
FIG. 8 shows the robustness assessment on the stability of LY-CH-derived mAb sample stored in an auto-sampler at 2-8° C. for up to 15 h.

We assessed the sample stability with multiple freeze/thaw cycles by comparing the results of the derivatized/buffer-exchanged oxi-standard mAb samples subjected to one, two, and three freeze (at −80° C.)/thaw cycles with that of the freshly prepared sample. The data (FIG. 7F) showed that the derivatized sample was stable against multiple freeze/thaw cycles. The stability of the derivatized sample for the HPLC analysis was assessed by measuring the carbonylation level of the derivatized and buffer-exchanged oxi-standard mAb stored in the HPLC autosampler (temperature controlled at 8° C.) for 1, 3, 5, 7, 9, 11, 13, and 15 h. In addition, as shown in FIG. 8, no significant difference in the measured carbonylation levels were observed, supporting that the derivatized samples are stable at 2-8° C. for at least 15 h.

Overall, a total of 31 data points were generated from the robustness assessment studies using the oxi-standard mAb as the test sample, showing an average total carbonylation level of 13.0 nmol/mg with a coefficient of variation (RSD) of 2.4%. These data support that CALY is highly robust.

Specificity Assessment

Specificity was investigated by subjecting the sample blank, which has all the sample buffer components except the mAb species, to the derivatization, the buffer exchange, and the SEC analysis steps. As shown in FIG. 3A and 3B, no peak was observed in the peak of interest region (from 10 to 22 minutes), which demonstrated that the buffer excipients do not interfere with the quantitation process and the CALY method is specific for measuring total protein carbonylation of mAb samples.

Limit of Detection and Limit of Quantitation

The limit of detection (LOD) and limit of quantitation (LOQ) were calculated respectively as 3 times and 10 times of the standard deviation of the carbonylation levels of a negative control. The standard deviation was determined to be 0.058 nmol/mg as shown in Table 1 by analyzing the unstressed and underived mAb as the negative control sample, with repeated injections (a total of 27 data points) at various protein concentrations. The LOD and LOQ for CALY were then determined to be 0.2 and 0.6 nmol/mg, respectively.

TABLE 1

Carbonylation levels from an unstressed mAb sample not derived by LY-CH as a negative control by repeated injections at various concentrations. The standard deviation from these data, 0.0581 nmol/mg, was used for determination of LOD and LOQ.

| Set | carbonylation Levels |
|---|---|
| 1 | 0.18 |
| | 0.2 |
| | 0.21 |
| | 0.2 |
| | 0.19 |
| | 0.2 |
| | 0.19 |
| | 0.19 |
| | 0.19 |

TABLE 1-continued

Carbonylation levels from an unstressed mAb sample not derived by LY-CH as a negative control by repeated injections at various concentrations. The standard deviation from these data, 0.0581 nmol/mg, was used for determination of LOD and LOQ.

| Set | carbonylation Levels |
|---|---|
| 2 | 0.15 |
|  | 0.16 |
|  | 0.16 |
|  | 0.15 |
|  | 0.17 |
|  | 0.15 |
|  | 0.16 |
|  | 0.16 |
|  | 0.16 |
| 3 | 0.06 |
|  | 0.08 |
|  | 0.09 |
|  | 0.05 |
|  | 0.04 |
|  | 0.05 |
|  | 0.05 |
|  | 0.05 |
|  | 0.09 |
| STD | 0.0581 |

Linearity and Precision

After the method optimization and the robustness studies, another batch of the oxi-standard mAb sample for the subsequent assessment was prepared. The total protein carbonylation level of the second batch was determined by CALY to be 11.5 nmol/mg, slightly lower than that of the first batch. However, this does not affect the subsequent method performance assessment on linearity and precision. For simplicity, the second batch oxi-standard mAb was referred to as the oxi-standard mAb (II) sample hereafter.

Figure 9:
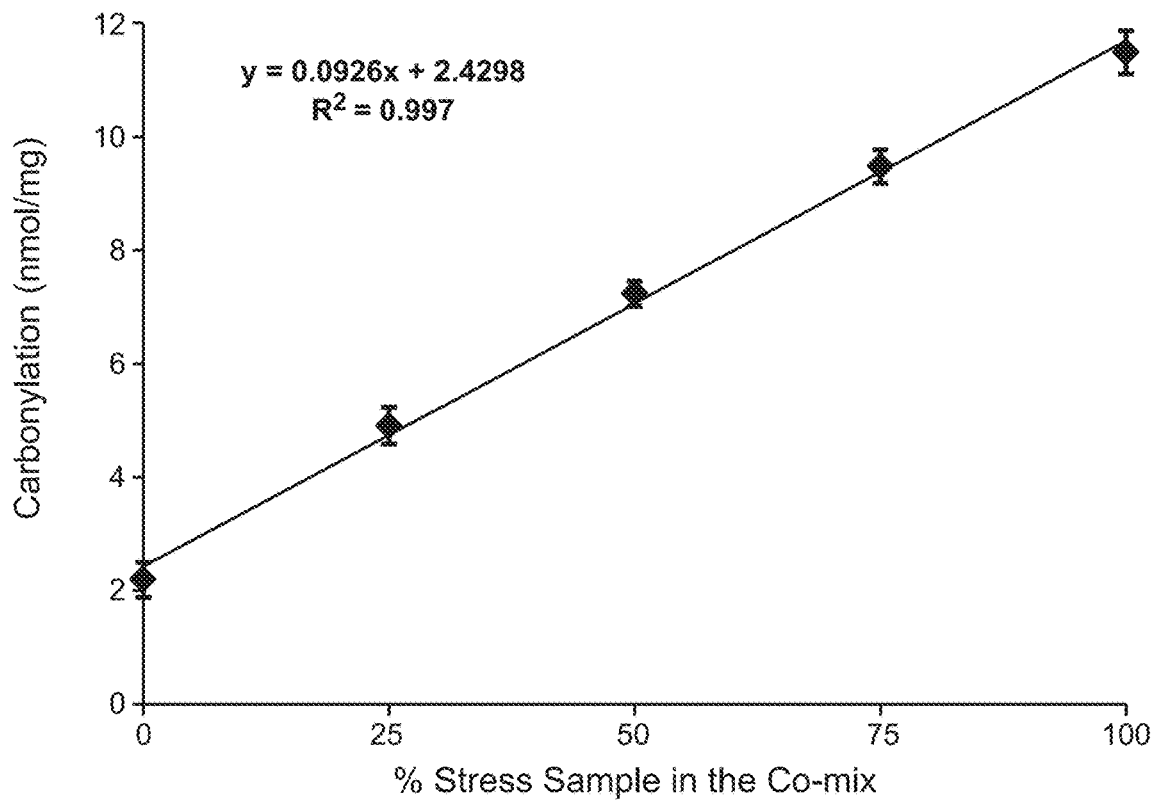
FIG. 9 shows the performance of the method on assay linearity and assay precision by the analysis of the co-mix samples by two analysts in three days and on two different HPLC instruments.

To assess the linearity of CALY, a series of co-mix samples by mixing oxi-standard mAb (II) with the unstressed mAb at 0-to-100, 25-to-75, 50-to-50, 75-to-25, and 100-to-0 (mass to mass) ratios was prepared. Subsequently, the co-mix samples were analyzed by two analysts, on two HPLC instruments, with two size exclusion columns and three independent preparations by each analyst, and on three different days. A total of six independent measurements were performed for each co-mix sample. As shown in FIG. 9, we observed a linear response for the measured total protein carbonylation in proportion to the percentage of stressed mAb in the respective co-mix samples, with a linear regression ratio of 0.997. This data demonstrated that CALY has excellent linearity. In addition, the coefficient of variation (CV) from the measurement from the intra-day and inter-day analyses from two analysts for each of the co-mix sample is below 15%, demonstrating the precision of CALY.

Example 5

Determination of Protein Carbonyl Levels of mAbs by the DNPH Colorimetric Assay

Figure 10:
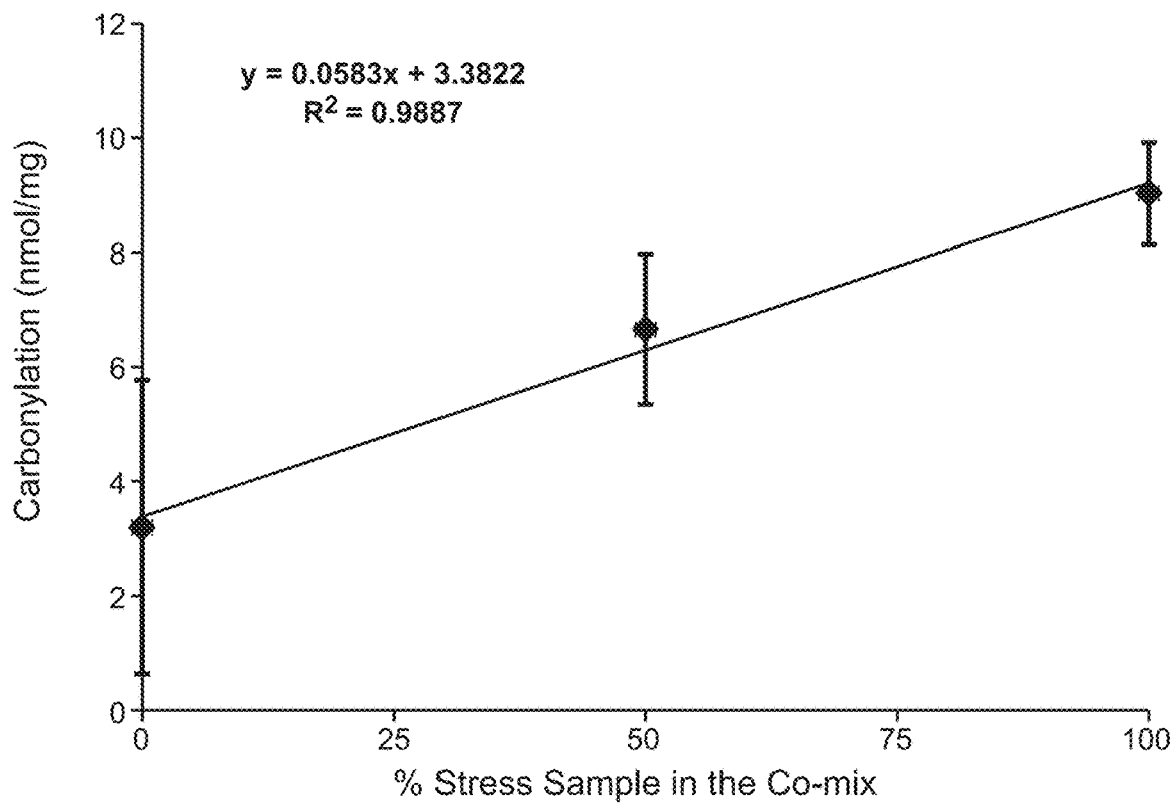
FIG. 10 shows the performance of the DNPH method on assay linearity and assay precision by the analysis of the co-mix samples.

The total protein carbonylation level for some mAb samples was also quantified by using the OxiSelect™ Protein Carbonyl Spectrophotometric Assay Kit (Cell Biolabs, Inc., San Diego, Calif.). Three independent preparations were performed to report an average protein carbonylation level for each sample.
Comparison to the DNPH Spectrophotometric Assay
The DNPH spectrophotometric assay is a conventional protein carbonylation assay. The total protein carbonylation levels were measured for the oxi-standard mAb (II), the 50:50 co-mix, and the unstressed mAb by the DNPH method and the CALY method to determine how close the results are by the two methods and to compare the performance of the two methods. Overall, as shown in FIGS. 9 and 10, the respective carbonylation levels determined from the two methods are similar, while the CALY method clearly demonstrated better assay precision than that from the DNPH method.

Example 6

CALY Analysis of the PNGase F Treated mAbs

Figure 11:
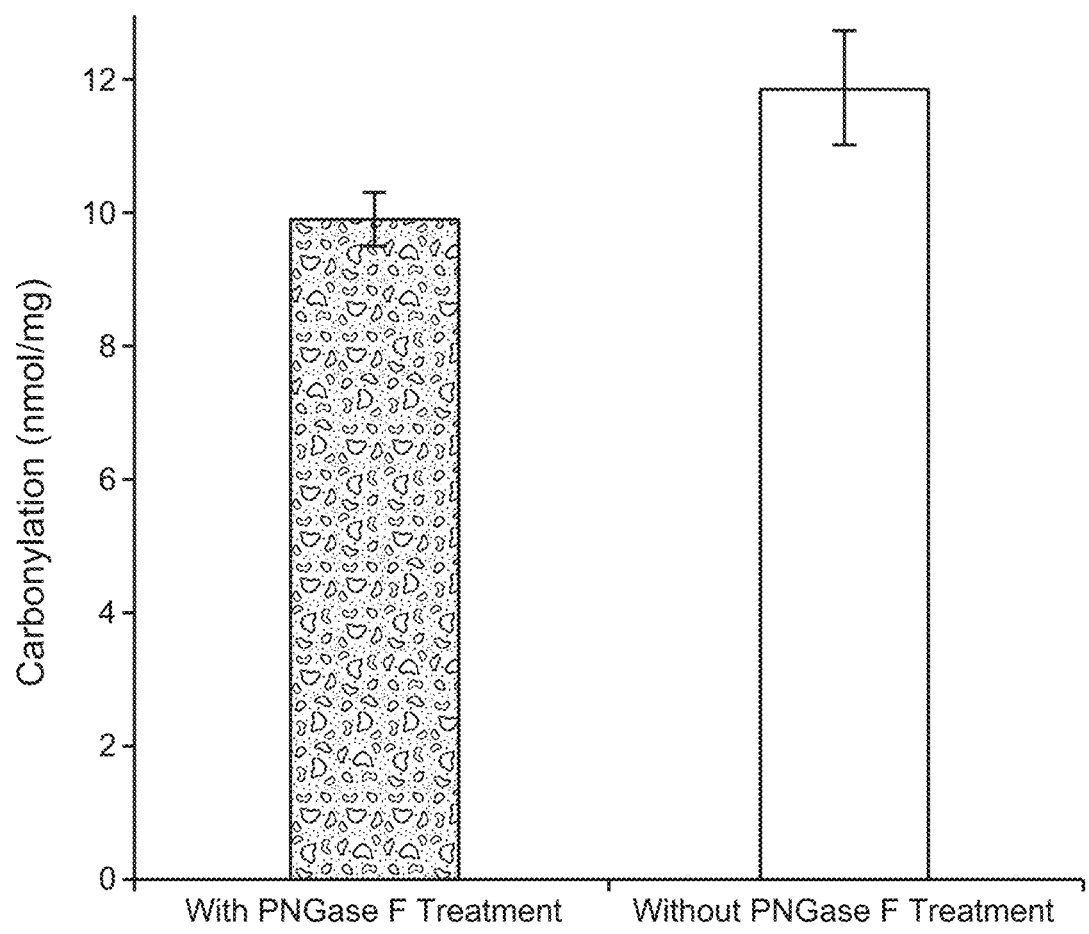
FIG. 11 shows the total protein carbonylation levels of an oxidized mAb sample with and without PNGase F treatment.

LY-CH has previously been used as a derivatization reagent to quantify aldehyde groups formed by periodic acid oxidation on the N-Glycan oligosaccharide residues of antibodies. Since the reactivity of LY-CH with the aldehydes and ketones on amino acid residues may not be the same as with the N-glycan aldehydes, it was evaluated if LY-CH was suitable for quantifying the metal-catalyzed oxidative carbonylation on the amino acid residues of mAbs. The total protein carbonylation level of the unstressed and the Fenton-stressed mAb samples with and without PNGase F treatment were measured by CALY. Since the PNGase F treatment removes the N-glycan from the mAb samples, the total protein carbonylation level of the mAb samples measured after the PNGase F treatment is attributed to the carbonylation on amino acid residues on mAbs. As shown in FIG. 11, the total protein carbonylation levels for the oxi-standard mAb (II) sample with and without PNGase F treatment were 9.9 nmol/mg and 11.9 nmol/mg, respectively. These data confirm the specific suitability of CALY on quantifying the metal-catalyzed carbonylation on amino acid residues. In addition, these data indicate that, under the Fenton's oxidation conditions tested in this study, no significant amount of N-glycan aldehyde was formed on the mAb sample.
Deglycosylation by PNGase F treatment
The deglycosylation reaction was conducted by mixing 250 μg of a mAb sample with 12500 units of PNGase F in 100 mM HEPES buffer, pH 8.0 to a final volume of 1 mL. The mixture was incubated at 37° C. for 16 h.

Example 7

Determination of Protein Carbonyl Levels of mAb Oxidized Using Various Amounts of Fe (II) and Hydrogen peroxide The mAb samples were prepared using a total of 16 conditions with combination of various final concentrations of Fe (II) (4 μM, 20 μM, 100 μM, and 500 μM) and hydrogen peroxide (8 μM, 40 μM, 200 μM, and 1000 μM) as shown in Table 2. The final mAb concentration was 5 mg/mL. The mixture was incubated at room temperature in a 50 mM sodium succinate buffer, pH 6.5, for 2 hours. Subsequently, the reaction was stopped by adding excess amount of methionine and EDTA.

Figure 12A:
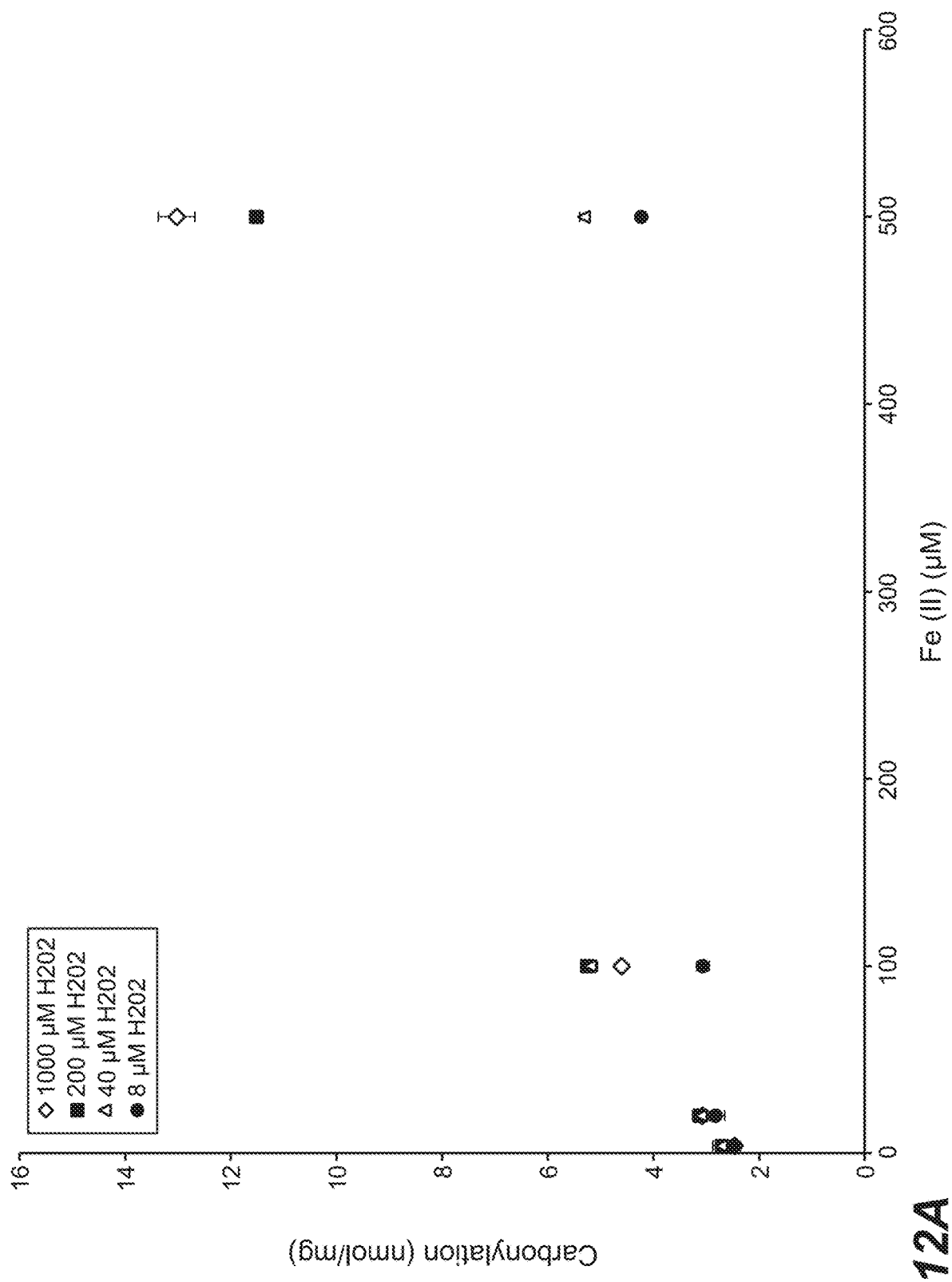
FIG. 12A shows the relationship between the resulting total carbonylation levels and the Fe (II).
Figure 12B:
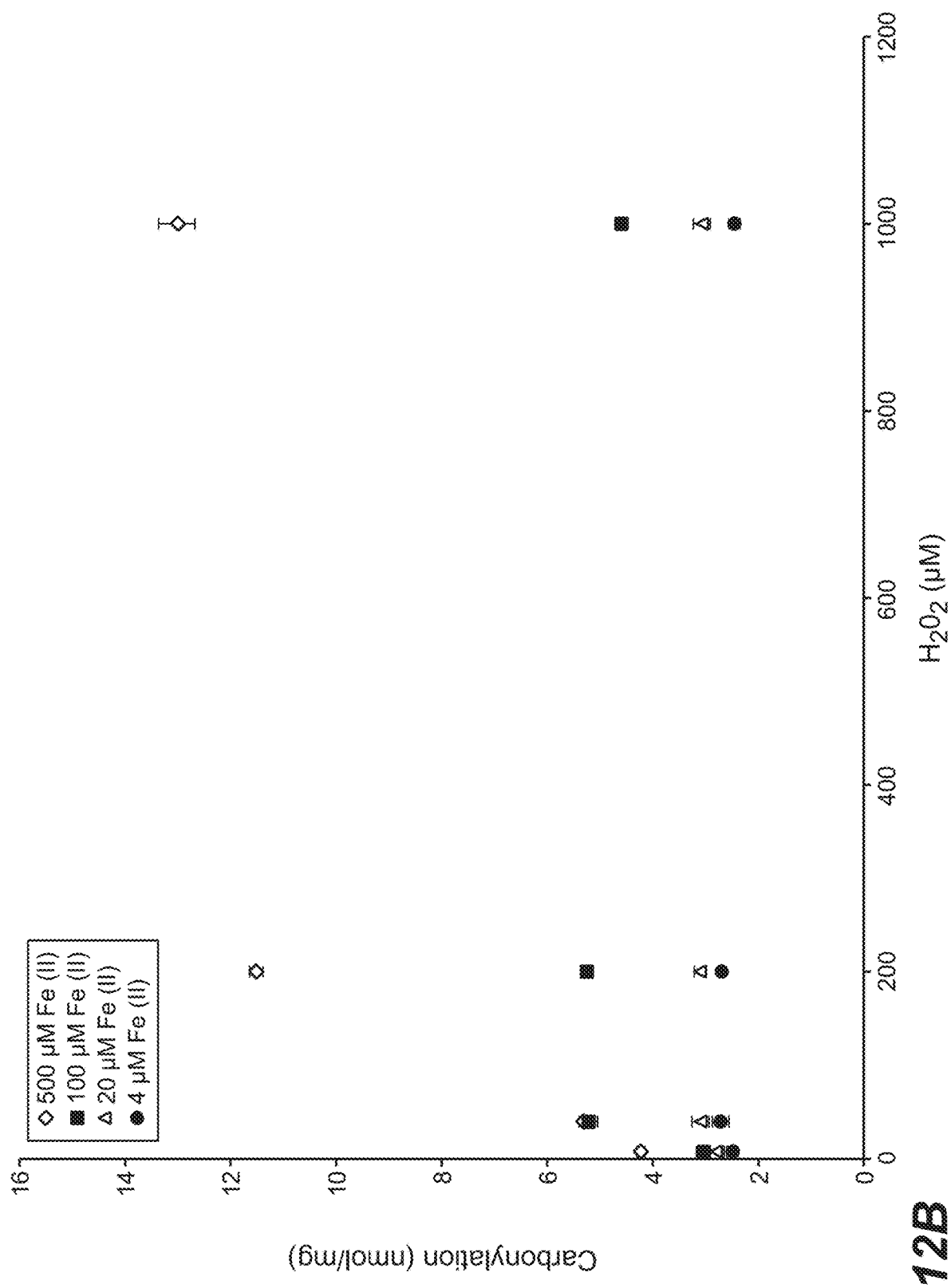
FIG. 12B shows the relationship between the resulting total carbonylation levels and hydrogen peroxide concentrations used for the metal-catalyzed oxidation.
Figure 12C:
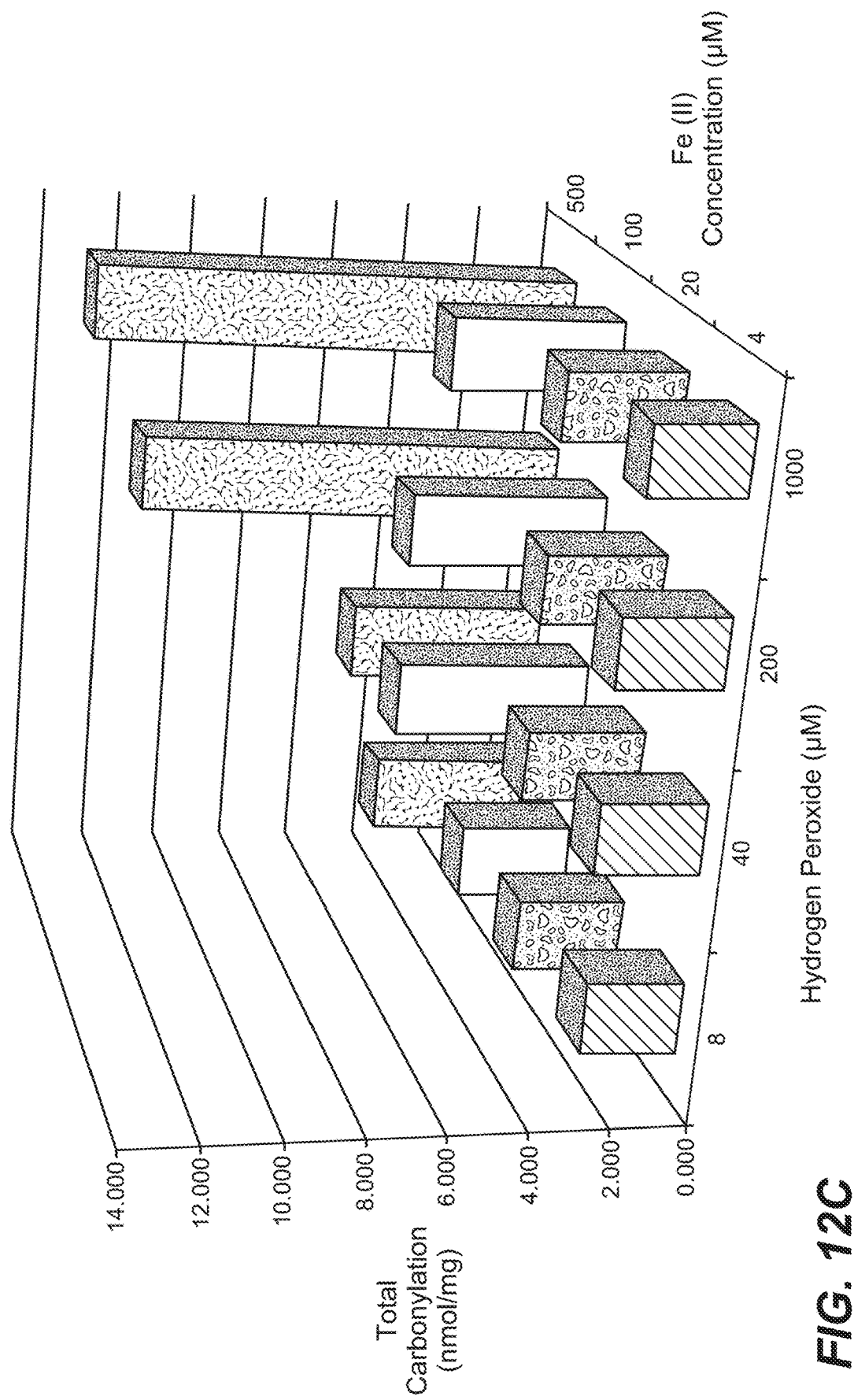
FIG. 12C shows the relationship between the total carbonylation levels, the Fe (II) and hydrogen peroxide concentrations used for the metal-catalyzed oxidation.

As shown in FIG. 12A, 12B and 12C, the effect of various amounts of Fe (II) and hydrogen peroxide on the total protein carbonylation levels are quite complicated. It was observed that at lower Fe (II) concentrations (4 μM and 20 μM), the total carbonylation level of the stressed mAb varies only slightly even with a wide range of hydrogen peroxide amounts (8 μM to 1000 μM). In contrast, for each hydrogen peroxide concentration tested, there was a consistent trend showing higher total carbonylation with higher concentrations of Fe (II) ranging from 4 μM to 500 μM. These data seem to suggest that, under these specified stress conditions, the extent of oxidative carbonylation is relatively more sensitive to changes in the metal ion concentration than that of hydrogen peroxide. Therefore Fe (II) may be a more critical factor than hydrogen peroxide for generating protein carbonylation on mAbs under these conditions.

TABLE 2

A total of 16 conditions with various Fe (II) and H2O2 concentrations (final); the final mAb concentration was 5 mg/mL; the oxidation was carried out at room temperature for 2 h and then quenched by adding excess amount of EDTA and methionine.

| Sample No. | mAb | Fe (II) | Hydrogen Peroxide |
|---|---|---|---|
| 1 | 5 mg/mL | 500 µM | 1000 µM |
| 2 | | | 200 µM |
| 3 | | | 40 µM |
| 4 | | | 8 µM |
| 5 | | 100 µM | 1000 µM |
| 6 | | | 200 µM |
| 7 | | | 40 µM |
| 8 | | | 8 µM |
| 9 | | 20 µM | 1000 µM |
| 10 | | | 200 µM |
| 11 | | | 40 µM |
| 12 | | | 8 µM |
| 13 | | 4 µM | 1000 µM |
| 14 | | | 200 µM |
| 15 | | | 40 µM |
| 16 | | | 8 µM |

Example 8

Determination of Protein Carbonyl Levels of mAb with PS20 Formulations and Low Levels of Fe (II) During Storage Polysorbate 20 (PS20) is a commonly used surfactant in antibody formulations to address antibody aggregation, but it is also known to contain peroxides (Jaeger et al., 1994). During storage of mAbs, the peroxides ENREF 39 from PS20 could react with iron ions to induce antibody carbonylation. To investigate the effect of PS20 and iron on mAb carbonylation during storage, mAb samples were prepared in 50 mM sodium succinate buffer (pH 6.0) with various final Fe (II) (0.1 µM and 0.8 µM) and PS20 (0.02% and 0.16%, w/v) concentrations as shown in Table 3. The PS20 concentrations are based on the reported PS20 concentration range in mAb formulations (Hawe et al., 2010). The Fe (II) concentrations are based on the concentration range of leached iron ions reported (Zhou et al., 2011). These samples were then stored at room temperature in the dark for 4, 8, and 16 weeks. At each time point, excess methionine and EDTA were added to the samples to quench the carbonylation reactions. Subsequently, these samples were stored at −80° C. until further analysis by CALY.

TABLE 3

A total of 5 conditions with various Fe (II) and PS20 concentrations (final) for the storage experiments. B1 was included as the control.

| Condition | Fe (II) | PS20 |
|---|---|---|
| B1 | 0 uM | 0% (w/v) |
| B2 | 0.1 uM | 0.02% (w/v) |
| B3 | 0.1 uM | 0.16% (w/v) |
| B4 | 0.8 uM | 0.02% (w/v) |
| B5 | 0.8 uM | 0.16% (w/v) |

Figure 13:
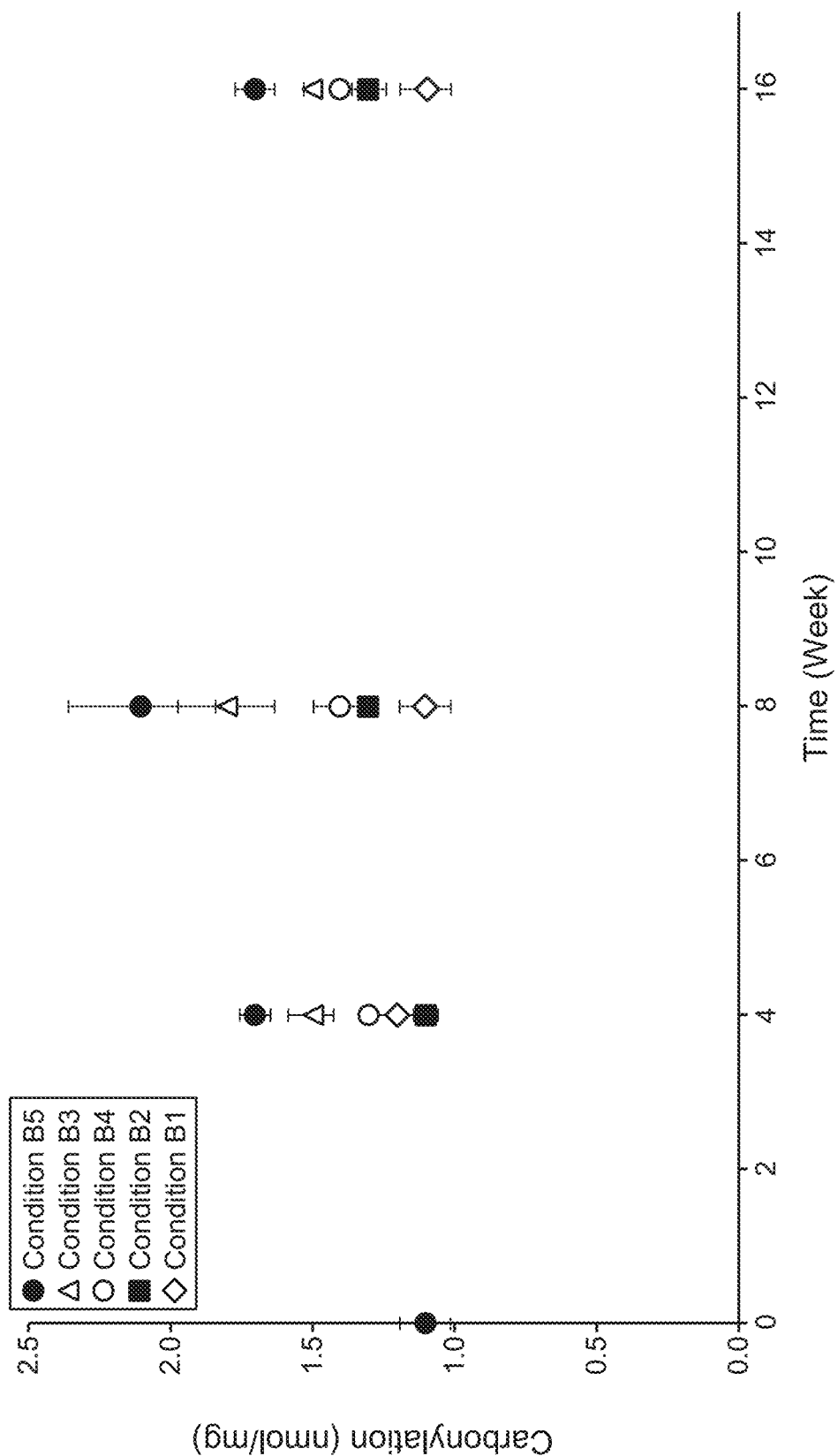
FIG. 13 shows the total protein carbonylation levels of mAb samples containing various amounts of Fe (II) (0.1 μM and 0.8 μM) and PS20 (0.02% and 0.16%, w/v) and stored at room temperature in the dark for 4, 8, and 16 weeks. Condition B5: 0.8 μM Fe(II) and 0.16% PS20; Condition B3: 0.1 μM Fe(II) and 0.16% PS20; Condition B4: 0.8 μM Fe(II) and 0.02% PS20; Condition B2: 0.1 μM Fe(II) and 0.02% PS20; Condition B1: without Fe (II) or PS20 (the control).

As shown in FIG. 13, for all four samples (B2 to B5) that contain PS20 and Fe (II), appreciable increase in the carbonylation level was observed during the storage. In comparison, no significant change in the carbonylation level was observed for the control sample (B1). These data showed that mAbs with PS20 formulations are susceptible to carbonylation when low levels of iron ions are present during storage. Interestingly, the samples with 0.16% PS20 (B5 and B3) had consistently higher levels of carbonylation than the samples with 0.02% PS20 (B4 and B2) at 4, 8, and 16 weeks, regardless of the iron concentrations. This observation indicates that PS20 had a major effect on mAb carbonylation in these cases. Thus, the hydroperoxides from PS20, the likely source of free radicals, became a more critical factor that limited the extent of mAb carbonylation under the storage conditions. The 0.16% PS20 formulations, which contain more hydroperoxides, therefore had consistently higher levels of protein carbonylation. This further shows that, in the presence of low levels of iron ions, the hydroperoxide content of surfactants could have a significant impact on mAb carbonylation during storage. Another interesting observation is that the carbonylation level of samples B3 and B5 decreased significantly from week 8 to week 16. The decrease in the carbonylation content of these samples shows that a decarbonylation process may exist.

REFERENCES

Buss H, Chan T P, Sluis K B, Domigan N M, Winterbourn C C. Protein carbonyl measurement by a sensitive ELISA method. Free radical biology & medicine. 1997; 23(3): 361-366.

Keener C R, Wolfe C A, Hage D S. Optimization of oxidized antibody labeling with Lucifer Yellow C H. Biotechniques. 1994; 16(5):894-897.

Levine R L, Garland D, Oliver C N, Amici A, Climent I, Lenz A G, Ahn B W, Shaltiel S, Stadtman E R. Determination of Carbonyl Content in Oxidatively Modified Proteins. Methods in Enzymology. Methods Enzymol. 1990; 186:464-478.

Matthijssens F B, Bart P.; Vanfleteren, Jacques R. Evaluation of Different Methods for Assaying Protein Carbonylation. Current Analytical Chemistry. 2007; 3(2):93-102.

Mesquita C S, Oliveira R, Bento F, Geraldo D, Rodrigues J V, Marcos J C. Simplified 2,4-dinitrophenylhydrazine spectrophotometric assay for quantification of carbonyls in oxidized proteins. Analytical biochemistry. 2014; 458: 69-71.

Mohanty J G, Bhamidipaty S, Evans M K, Rifkind J M. A fluorimetric semi-microplate format assay of protein carbonyls in blood plasma. Analytical biochemistry. 2010; 400(2):289-294.

Morehead H W, Talmadge K W, O'Shannessy D J, Siebert C J. Optimization of oxidation of glycoproteins: an assay for predicting coupling to hydrazide chromatographic supports. J Chromatogr. 1991; 587(2):171-176.

Rogowska-Wrzesinska A, Wojdyla K, Nedic O, Baron C P, Griffiths H R. Analysis of protein carbonylation—pitfalls and promise in commonly used methods. Free Radic Res. 2014; 48(10):1145-1162.

Uehara H, Rao V A. Metal-mediated protein oxidation: applications of a modified ELISA-based carbonyl detection assay for complex proteins. Pharm Res. 2015; 32(2): 691-701.

Yan L J, Forster M J. Chemical probes for analysis of carbonylated proteins: a review. J Chromatogr B Analyt Technol Biomed Life Sci. 2011; 879(17-18):1308-1315.

Stadtman, E. R. "Metal ion-catalyzed oxidation of proteins: biochemical mechanism and biological consequences." Free Radic Biol Med. 1990; 9(4): 315-325.

Bai Y, Wu C, Zhao J, Liu Y H, Ding W, Ling W L. "Role of iron and sodium citrate in animal protein-free CHO cell culture medium on cell growth and monoclonal antibody production." Biotechnol Prog. 2011; 27(1): 209-219.

Mallaney M, Wang S H, Sreedhara A. "Effect of ambient light on monoclonal antibody product quality during small-scale mammalian cell culture process in clear glass bioreactors." Biotechnol Prog. 2014; 30(3): 562-570.

Halliwell B, Clement M V, Ramalingam J, Long L H. "Hydrogen peroxide. Ubiquitous in cell culture and in vivo?" IUBMB Life. 2000; 50(4-5): 251-257.

Jaeger J, Sorensen K, Wolff S P. "Peroxide accumulation in detergents." J Biochem Biophys Methods. 1994; 29(1): 77-81.

Hawe A, Filipe V, Jiskoot W. "Fluorescent molecular rotors as dyes to characterize polysorbate-containing IgG formulations." Pharm Res. 2010; 27(2): 314-326.

Zhou S, Schöneich C, Singh S K. "Biologics formulation factors affecting metal leachables from stainless steel." AAPS PharmSciTech. 2011; 12(1): 411-421.

What is claimed is:

1. A method for determining a total carbonylation level on a polypeptide wherein the method comprises the steps of
    a) Contacting the polypeptide in a solution with a hydrazide dye under conditions which cause the hydrazide dye to react with a carbonyl group present on an amino acid residue of the polypeptide to form a polypeptide-dye-complex in a resultant solution from step a),
    b) Removing unbound hydrazide dye from the resultant solution from step a) to form a resultant solution from step b),
    c) Determining in the resultant solution from step b) a concentration of the hydrazide dye bound in the polypeptide-dye-complex and a concentration of the polypeptide bound in the polypeptide-dye-complex, and
    d) Determining the total carbonylation level of the polypeptide based on a ratio of the concentration of the hydrazide dye bound in the polypeptide-dye-complex to the concentration of the polypeptide bound in the polypeptide-dye-complex;
    wherein the hydrazide dye is Lucifer Yellow carbohydrazide (LY-CH);
    wherein step a) is performed in the presence of alkali metal ions.

2. The method according to claim 1, wherein the alkali metal ions are selected from lithium ions, sodium ions and potassium ions.

3. The method according to claim 1, wherein the alkali metal ions are lithium ions.

4. The method according to claim 1, wherein the amino acid residue of the polypeptide is selected from the group consisting of arginine, lysine, proline and threonine.

5. The method according to claim 1, wherein the polypeptide is an antibody.

6. The method according to claim 5, wherein the antibody is a polyclonal antibody, a monoclonal antibody, a humanized antibody, a human antibody, a chimeric antibody, a multi-specific antibody, an antibody fragment, or an antibody drug conjugate.

7. The method according to claim 1, wherein the polypeptide and the hydrazide dye is contacted in step a) in a final molar ratio of 6,000-10,000.

8. The method according to claim 1, wherein step a) is performed in the presence of a non-ionic surfactant.

9. The method according to claim 8, wherein the non-ionic surfactant is reduced Triton X-100.

10. The method according to claim 1, wherein step a) is performed at a temperature of 35° C.-39° C.

11. The method according to claim 1, wherein step a) is performed for 10-20 h.

12. The method according to claim 1, wherein step b) is performed by a method selected from the group consisting of filtration, gel filtration and dialysis.

13. The method according to claim 1, wherein step b) is performed by filtration.

14. The method according to claim 13, wherein filtration is carried out in the presence of 100-300 mM potassium phosphate and in the presence of 200-300 mM potassium chloride.

* * * * *